United States Patent [19]

Hyman

[11] Patent Number: 4,992,365

[45] Date of Patent: Feb. 12, 1991

[54] METHOD OF DETECTING BACTERIA IN URINE

[76] Inventor: Edward S. Hyman, 3420 Jefferson Ave., New Orleans, La. 70125

[21] Appl. No.: 205,959

[22] Filed: Jun. 13, 1988

Related U.S. Application Data

[63] Continuation-in-part of Ser. No. 31,771, Mar. 30, 1987, abandoned, which is a continuation-in-part of Ser. No. 603,088, Apr. 23, 1984, Pat. No. 4,673,637.

[51] Int. Cl.$^5$ .......................... C12Q 1/04; G01N 1/00
[52] U.S. Cl. .......................................... 435/34; 435/29; 435/39; 435/18; 436/501; 436/175; 436/177; 436/178; 424/3
[58] Field of Search ..................... 435/29, 34, 39, 825, 435/18; 436/175, 177, 178; 424/3

[56] References Cited

U.S. PATENT DOCUMENTS 3,926,727  12/1975  Vairel et al. .......................... 195/63
4,264,766  4/1981  Fisher ................................... 536/51

Primary Examiner—Esther L. Kepplinger
Assistant Examiner—Toni R. Scheiner
Attorney, Agent, or Firm—Nixon & Vanderhye

[57] ABSTRACT

New and substantially improved methods for the detection of bacteria, bacterial fragments and/or bacterial antigens are described. Novel methods for treatment of rheumatoid arthritis, "essential" hypertension and a variety of diseases found to be associated with bacteriuria are also described. Additionally, the specification discloses that the new and improved methods for direct microscopic examination are advantageously used for examination of formed elements in samples of other body fluids.

26 Claims, 2 Drawing Sheets

METHOD OF DETECTING BACTERIA IN URINE

CROSS REFERENCE TO RELATED APPLICATIONS

This application is a continuation-in-part of application Ser. No. 031,771 filed Mar. 30, 1987, now abandoned, which in turn is a continuation-in-part of application Ser. No. 603,088, filed on Apr. 23, 1984, now U.S. Pat. No. 4,673,637, which is incorporated herein by reference.

This invention relates to new and improved methods for the detection of bacteria in urine; to the discovery of such heretofore unknown bacteria in the urine of patients suffering from rheumatoid arthritis and related autoimmune diseases, hypertension, and other diseases; and to the treatment of these diseases as a result of the discovery of the presence of said bacteria. The methods are also applicable to the detection of bacteria in other body fluids, e.g. pleural fluid, peritoneal fluid, cerebrospinal fluid, synovial fluids, etc., and to the examination of formed elements (cytology) in urine and in such other body fluids.

This invention also relates to methods for the preservation of urine samples for the detection of bacteria at a later date.

BACKGROUND OF THE INVENTION

1. Conventional methods for Detecting bacteria in Urine

Urine originates as an ultrafiltrate of plasma and is normally thought to be free of bacteria as it moves from the upper urinary tract to the bladder. Therefore, bladder urine obtained by suprapubic needle aspiration, and perhaps urine properly obtained by a catheter inserted via the urethral meatus, should contain no bacteria. As it is voided from the body however, the urine is frequently contaminated with microorganisms which colonize the distal urethra and/or the perianal area. The most common non-invasive method of obtaining urine samples which attempts to minimize, but rarely completely eliminates contamination involves meticulous swabbing of the urethral meatus and periurethral areas with a bactericidal agents, followed by the collection of a mid-stream "clean-catch" specimen. By current teaching, the specimen should be examined within 1 hour of collection (two hours if the unpreserved urine specimen is refrigerated) to obviate proliferation of bacteria. Although most contaminating microorganisms are avoided by this "clean-catch" method, the collected samples may still contain some contaminants.

Quantification of the viable bacteria has been the essential parameter used for determining the presence of "significant" (i.e. clinically relevant) bacteriuria. Today it is generally accepted that "clean-catch" urines which on culture are shown to contain: (1) $10^5$ colony-forming-units per ml (cfu/ml) represent true urinary tract infection (i.e., "significant bacteriuria"); (2) from $10^3$ to $10^5$ cfu/ml represent probable infection (varying with the author); and (3) less than $10^3$ cfu/ml represent probable contamination. Although "significant" bacteriuria refers to at least the presence of $10^5$ cfu/ml of urine, consistent findings of $10^4$–$10^5$ cfu/ml probably represent more than mere colonization if the distal urethra, particularly if only a single species of organism is present.

Traditionally, direct microscopic examination of urine to detect and to approximate the number of bacteria in specimens has been performed according to four general methods. As described by C. Cobbs (in Urinary Tract Infection and Its Management, D. Kaye, ed., C. V. Mosby Company, St. Louis, Mo., ch. 4, pp. 43–44), these include: (1) A small sample of uncentrifuged urine is spread on a slide, covered with a cover slip, and examined with the high dry objective (at 400X magnification) i.e., a wet mount preparation). A dye such as methylene blue may be added to the urine to enhance visibility of the bacteria. (2) A small sample of uncentrifuged urine is placed on a slide, heat-fixed, stained, e.g., using Gram stain, and examined with the high dry objective (at 400X magnification) or under oil immersion (at 1000X magnification). (3) A known volume of urine is centrifuged, the sediment resuspended in the residual fluid. A small sample of the sediment is spread on a slide, covered with a cover slip, and examined directly using the high dry objective (i.e., a wet mount slide preparation). (4) The centrifuged urine sediment is prepared as in (3) above, but the sample is heat-fixed, stained, e.g., using Gram stain, and examined with the high dry or under oil immersion objective. Using the above methods, detection of one or more bacterial organisms per microscopic field has been correlated with the minimum bacterial counts obtained by conventional culture of urine samples according to Cobbs' data illustrated in Table I.

TABLE I

| Urine Sample | Bacteria Observed Field | Magnification | Correlation with Bacteria on Culture |
|---|---|---|---|
| Unstained Uncentrifuged | 1 Organism or more | 400 × | $10^6$ per ml. |
| Stained Centrifuged | 1 Organism or more | 1000 × | $10^5$ per ml. |
| Unstained Centrifuged | 1 Organism or more | 400 × | $10^5$ per ml. |
| Stained Centrifuged | 1 Organism or more | 1000 × | $10^4$ per ml. |

Under good conditions bacteria may be seen in an aqueous medium under the microscope at as low at 100 diameters or less magnification, but they are usually visualized at 1000 diameters magnification after drying and staining with appropriate dyes. In the past both methods of visualization have been used to examine urine for the presence of bacteria. Using conventional wet mount slide preparations, bacteria usually observed in urine are Gram negative bacilli (rods). Group D streptococci are also seen in classical urinary tract infections (Todd et al., 1984, in Clinical Diagnosis and Management by Laboratory Methods 17th ed., Henry, ed., W. B. Saunders, N.Y.).

Much more commonly bacteria are demonstrated in urine by allowing the bacteria to grow in a designated culture medium until the colonies are visible to the naked eye. By counting the colonies and multiplying by the dilution of the urine, and by assuming that one colony consists of the progeny of a single bacterium (or a small cluster of bacteria such as a pair) in the original specimen, the number of bacteria (or more accurately, colony forming units of bacteria) in a given volume of urine may be estimated.

Using conventional urine culture techniques, it has been uniformly reported since Kass in 1956 (Transactions of the Association of American Physicians, 69, 56–64) that the Gram negative bacillus E. coli. is the most common causative agent in acute urinary tract infections. In chronic urinary tract infections, especially those in which there are structural abnormalities (e.g., obstructive uropathy, congenital abnormalities, neurogenic bladder, fistulous communications involving the urinary tract etc.), infection is often associated with antimicrobial-resistant Gram negative bacilli such as *E. coli, Proteus sp., Pseudomonas sp.*, and the Klebsiella-Enterobacter group. Finally, largely as a result of technology, urinary tract infections are associated with the presence of Gram negative rods such as *E. coli, Proteus,* the Klebsiella-Enterobacter group, and a lesser number of cocci such as *Staphylococcus epidermidis,* and the *enterococcus.*

In the literature since Kass in 1956, Gram positive organisms are much less frequent as causative agents than are Gram negative bacilli, and they are often observed as "contaminants" because they yield low colony counts. This skewing against the incidence of Gram positive organisms has been made worse by the selection of culture media for routing laboratory use. Since the incidence of Gram negative rods had been reported to be higher, media have been selected to favor the rapid growth of Gram negative rods at the expense of Gram positive cocci, and this selection of media has further distorted the incidence.

Direct microscopy and culture methods each have disadvantages. With regard to the direct examination of the urine, it must be noted that bacteria may be seen in urine at only 100 or more diameters magnification, but the size of the image is not the only consideration influencing visibility. Should the optical density and refractive index of an object be near that of the medium, then it would not be detected by an ordinary light microscopy. Such an object might be seen by appropriate staining with dyes or by specialized lighting such as dark-field illumination, phase illumination, or differential interference. Even then, as pointed out by Kunin (1961, New Eng. J. Med. 265: 589), round bacteria cannot be distinguished from other near round particles such as crystals. Moreover, in a staining procedure, if for any reason the bacterial preparation does not adhere to the slide, the preparation is lost.

In the past 20–25 years, direct visualization of bacteria in urine has largely been abandoned in favor of methods involving culturing and counting the colonies of bacteria. Indeed, virtually all of the studies of the significance of bacteriuria since 1956 are based upon culturing the urine, and direct microscopic examination of urine has been relegated to the status of a quick but inadequate screening procedure which may be helpful because it is rapid and can be correlated with the culture methods.

Any useful culture method requires that the bacteria will grow in the laboratory in the medium selected and in the time allotted. If the medium used is inappropriate for the growth of the particular organisms present, they will not grow. If the time allotted is too short, colonies will not be visible and positive cultures may be mistakenly reported as negative; and if oxygen tension or oxidation potential is either too high or too low, fastidious anaerobic or aerobic organisms may be missed.

If the bacteria are dead when excreted from the body, then they will not grow. Dead bacteria were once alive, and dead ones in the urine were probably alive in the body. They are unable to multiply in the bladder, an important consideration in Kass' rule of $10^5$ cfu/ml. In addition, there are many reasons why bacteria in urine might display less than optimal viability. For example, the ionic strength or osmolarity of the urine may be outside the requisite range. The wall of the bacterium may be damaged so that it will require a special medium to grow. The oxidation potential potential of urine may be too high for growth of a particular bacterial species (e.g., the typical oxidation potential of urine observed by me is about $+0.22 + 0.25$ Volts, referenced to a saturated calomel electrode. This potential is sufficiently high to inhibit the growth of many bacteria). There may be agents in urine which inhibit bacterial growth. For example, antibodies against bacteria have been identified in urine and they have been demonstrated to be deposited on bacteria in urine. Moreover, antibiotics administered to a patient may be excreted in urine in active form at a higher concentration than in other body fluids. The more concentrated antibiotic or antibiotic metabolite is likely to inhibit bacterial growth. Urea (and perhaps other metabolites) present in all urine inhibits bacterial growth. Any one or a combination of these factors may inhibit or diminish bacterial grown in vitro.

U.S. Pat. No. 4,225,669, issued on Sept. 30, 1980 to Melnick et al., describes methods for semi-quantitative and semi-qualitative detection of bacteria in fluid specimens including urine, blood, water, samples and pharmaceutical products. The methods employ compositions of chelating agents and basic dyes capable of staining bacteria at pH of 7 or greater and observing the stained bacteria with the naked eye. Neither culture nor microscopic examination of bacteria is necessary. By intention and design, Melnick's method is referenced to the cultures and is used as a screening procedure prior to culture.

2. Rheumatoid Arthritis

Rheumatoid Arthritis (RA) is a chronic systemic inflammatory disease generally regarded as an autoimmune disorder. In addition to inflammation of joints, the disease may cause inflammation and damage to arteries (arteritis), nerves (neuropathy) the sclera of the eye (scleritis), the outer layer of the heart (pericarditis), cardiac muscle (myocarditis), lymph nodes (lymphadenitis), and subcutaneous connective tissue resulting in formation of rheumatoid nodules. The disease occurs worldwide.

The etiology of RA is unknown. During the past century, microbial infections have been postulated as the cause (See, e.g., D. C. Demonde, ed., 1976, Infection and Immunity in the Rheumatic Diseases, Blackwell Scientific Publications, London, pp. 95–287). Indeed some specific non-RA diseases having features resembling RA have been shown to be due to a specific microbe, e.g., Lyme Arthritis is caused by a spirochete.

However, until the present invention, the evidence for microbial causation of RA was, at best, inconclusive (See, e.g., D. J. McCarty et al., ed., 1979 Arthritis and Allied Conditions: A Text book of Rheumatology, 9th ed., ch. 28, p. 417; R. G. Petersdorf et al., 1983, Harrison's Principles of Internal Medicine, Part Six, ch. 346, McGraw Hill, New York, p. 1977; P. D. Utsinger, N.J. Zvaifler, and G.E. Ehrlich eds., Rheumatoid Arthritis, J. B. Lippincott Co., 1985, especially Ch.1, pg. 4 under "Focal Sepsis", Ch.2, pp. 12–13, and Ch.3, pp. 21–22). In these references, the streptococcus, found consistently in the urine of arthritics using this invention, has in the past been specifically entertained and denied as a causative agent because neither the germ itself nor its immunologic fingerprints have been consistently found in arthritis. Moreover, bacteriuria has not been associated with RA, and indeed one authority remarks "Urinary abnormalities are relatively uncommon in RA . . . . Urinary tract infection was not found to be increased in RA patients." (McCarty et al., supra, ch. 23, p. 499.)

3. Hypertension

Hypertension is a chronic elevation of blood pressure which is either without apparent cause (i.e., "essential" hypertension), or which results from a kidney disorder such as partial obstruction of the flow of blood to part or all of the kidney or a kidney infection (i.e., secondary hypertension). That secondary hypertension may be associated with a kidney infection (pyelonephritis) has been recognized at least since 1939 (see S. Weiss and F. Parker, Medicine, 19, 221–315, 1939). At present, however, the prevailing belief is that there is no strong correlation between "essential hypertension" and pyelonephritis, or even between hypertension and "asymptomatic" bacteriuria (i.e., bacteriuria without any symptom or other evidence of a kidney disorder). According to N. M. Kaplan (1982, in Clinical Hypertension, 3d. ed., p. 14), using conventional methods, bacteriuria is found in only 2–5% of hypertensives. The finding of bacteriuria in most of these studies has been dependent upon the conventional culture methods, and most of the bacteria found have been Gram negative rods.

BRIEF SUMMARY OF THE INVENTION

The present invention presents new and improved methods for detecting and identifying bacteria, bacterial fragments and/or bacterial antigens in samples of body fluids, e.g., urine. The present invention proposes improved methods for the preparation of samples for rapid direct microscopic detection, identification, and quantification of bacteria; the preservation of urine samples preparatory for delayed detection and identification of bacteria; rapid, quantitative methods and assay kits employing monoclonal or polyclonal antibodies or other reagents specific for bacteria and/or bacterial antigens herein shown to be associated with rheumatoid arthritis, "essential hypertension", and other related diseases; the administration of antibiotics effective against such detected and identified bacteria for the treatment of the above defined diseases; and the use of the system of detection to monitor the in-vivo effect of said antibacterial agents.

By virtue of the improved methods herein contemplated, it has been demonstrated that certain diseases of hitherto unknown or uncertain etiology are associated with bacteriuria not detected by prior methods. These bacteria are generally Gram positive cocci, although the now- classic pyelonephritis due to Gram negative rods is also readily detected by the methodology reported herein. Application of antibiotic therapy appropriate for the organisms detected not only diminishes the detected and identified bacteriuria but also offers therapeutic benefit for the associated disease. This therapeutic benefit or clinical improvement resulting from use of an agent whose primary effect is its antibacterial activity establishes a cause and effect relationship between the bacteria detected and the associated disease.

The present invention also presents novel methods for treatment of a variety of diseases found to be associated with bacteriuria according to the present invention. These include but are not limited to: Reiter's disease, ankylosing spondylitis, bursitis, tendonitis, tempero-mandibular arthritis, sacro-iliac arthritis, carpal-tunnel syndrome, temporal arteritis, palindromic rheumatism, and the recently defined Chronic Fatigue Syndrome (see G. P. Holmes, J. E. Kaplan, N. M. Gantz, et al., Chronic Fatigue Syndrome: A working Case Definition, Annals of Internal Medicine, vol. 108, 387–389, 1988). These diseases also include classic migraine, osteoarthritis with pain, Crohn's disease, "essential" hypertension, and the mitral valve prolapse syndrome (with or without associated "transient ischemic attacks" involving the central nervous system (or CNS), and with or without arrhythmias of the heart), and undoubtedly other illnesses to be encountered.

It is also believed that the methods of the present invention can be applied to the treatment of other diseases or conditions which include the following: rheumatic fever, systemic lupus erythematosis, scleroderma, dermatomyositis, transient ischemic attacks of the CNS, and glomerulonephritis in various stages. Classic bacteremia (or septicemia) may cause bacteriuria which is rapidly detectable by this new method.

Using the new and improved methods of detection of the present invention, bacteria, generally Gram positive cocci, have been found in the urine of patients suffering from a variety of renal disorders including renal failure due to congenital polycystic kidneys; renal failure due to otherwise unclassified chronic nephritis"; "brittle" diabetes mellitus; recurring kidney stones; unexplained proteinuria; unexplained edema; and chronic brawny edema (i.e., lymphangiitis or elephantiasis not due to non-bacterial parasites). Treatment of these patients with known antibacterial agents sufficient to reduce or eliminate the bacteriuria, benefited these patients as if they had been suffering the now-classic pyelonephritis, but often even more than if they had that entity.

Using the new and improved methods of detection of the present method, bacteriuria has also been demonstrated in patients suffering unexplained sever abdominal pain, proved mesenteric lymphangiitis, unexplained fatigue, and unexplained headaches. Treatment of these patients with antibiotic agents resulted in not only a decrease in the number of bacteria in the urine but also improvement of their clinical symptoms of unexplained etiology. It is believed that such patients suffer a bacterial infestation at some undisclosed body site.

The bacteria, dead or alive, whole or partial, eliminated in the urine of patients, have been detected in the urine of patients suffering from the above enumerated disorders by the novel methods of the present invention. Thus, it appears that the scope of illnesses which are associated with previously undetected bacteriuria is not limited by the boundaries of the conventional classification of illnesses.

The present invention describes rapid and novel methods for determining the presence of live or dead bacteria or bacterial fragments in the urine. The methods described herein are useful as a general diagnostic technique. They can be utilized in the diagnosis of illnesses, and to monitor the effectiveness of antibacterial agents and their dosages in the treatment of the above-listed diseases or conditions. They are particularly useful for the detection of bacteria which are not reliably detected by conventional methods.

Once the bacteria have been found and identified, an amount of an antibiotic effective against the bacteria is administered. The amount necessary is determined by the response of the bacteriuria, an in-vivo test of the agent. Relatively large doses of antibiotic may be necessary. For example, an oral dose of 600 mg. per day of clindamycin is sometimes effective, but doses of 3 to 8.4 grams a day by vein may be necessary to reduce or eliminate the bacteria, the dose being limited by the tolerance or the host for the chemical. The dosages may be adjusted for other routes of administration. It may be necessary to use combinations of antibacterial agents at one time to reduce or eliminate the bacteriuria as monitored by the method herein disclosed, e.g., clindamycin has been used with gentamycin, tobramycin, piperacillin, one of several cephalosporins, tetracyclines, chloramphenicol, etc.

Typically, when cocci have been found in urine by the method of this invention, antibiotic therapy has effectively reduced or eliminated the cocci and has alleviated the symptoms, signs, and often the abnormal laboratory findings of the patient.

One object of the invention is to detect bacteria in urine that are not detected by conventional methods.

Another object of the invention is to detect bacteria rapidly so that the method may be useful as a clinical test.

Another object of the invention is to ensure that all bacteria and formed parts of bacteria in a urine sample are collected in the sediment. According to one embodiment of the present invention, this is ensured by adequate centrifugation.

Another object of the invention is to ensure retention of the urine sediment on the microscope slide throughout staining.

Another object of the invention is to remove conflicting, extraneous, or interfering material from the sediment in the preparation of a slide.

Another object of the invention is to alert the physician to the possibility that antibiotic therapy, appropriate for the organisms found in the urine by the new and improved methods of this invention, might improve the patient's condition.

Another object of the invention is to provide therapeutic relief in cases of rheumatoid arthritis, "essential" hypertension, and other diseases or conditions found by methods described herein to be associated with significant bacteriuria.

Other objects will be apparent to a person of ordinary skill in the art after studying the specification and claims.

BRIEF DESCRIPTION OF THE FIGURES

The present invention may be more fully understood by reference to the following detailed description of the invention, examples of clinical histories demonstrating treatment according to novel methods of the invention and the appended figures in which.

DETAILED DESCRIPTION OF THE INVENTION

I

Improved Methods for Direct Microscopic Examination of Urine Samples

Urine samples - preservation: According to one embodiment of the present invention, bacteria in urine are detected by direct microscopic examination using the methods presented schematically in FIG. 1.

Step 1

Urine samples may be processed either fresh (i.e., within about one hour and preferably within about 20 minutes after collection) or preserved. Preservation of urine samples is accomplished by addition of about 1% by volume "liquefied phenol" (i.e., phenol containing sufficient water to render it liquid at room temperature), or by adding 0.1% sodium azide. In order to be able to rapidly identify preserved samples, it is preferable to add a trace amount of a proton sensitive vital stain such as tetra-brom phenolphthalein ethyl ester potassium salt and sufficient methanol to obtain a blue-green color. This also stains sediment. Other preservatives have been successfully used.

Step 2

Adjustment of pH: If the pH of the urine sample is greater than about 6, small aliquots of acetic acid are added dropwise to adjust the pH to about 6 or lower (preferably 5.0).

Step 3

Figure 2:
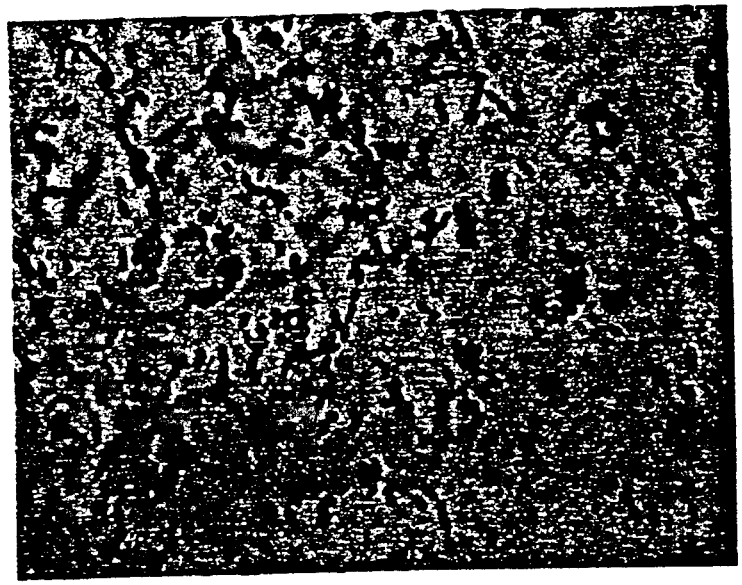
FIG. 2 is a photograph at 1000 diameters magnification of "exploded cocci" prepared and stained according to the present invention.

Centrifugation: Preferably, the urine is centrifuged at about 3000–11,000 times gravity for 10–15 minutes. Although slight improvement can be had at a higher centrifugal force, this is an adequate sedimentation force x time for urinalysis according to the present invention. Some novel bacterial forms disclosed herein may require centrifugation at 4000 × g or more. For example, FIG. 2 shows the "exploded" cocci sedimented at 4000 × g × 10 minutes. Centrifugal sedimentation forces lower than the preferred range (e.g., less than about 3000 × g) generally are not adequate to sediment some bacteria or bacterial fragments in urine particularly when the urine has a relatively high specific gravity, e.g., about 1,030.

In conventional methods for preparation of urine samples for microscopic examination, urine is centrifuged at a force of about 1000 times gravity or even less. Usually in publications dealing with this topic, the centrifugal force is not specified, is ambiguously stated, or is specified as so many revolutions per minute of a given centrifuge. Typically, when it can be determined, a force of about 1000 times gravity has been applied for about 5 minutes. Therefore, centrifugation of samples in the past has often been inadequate. Theoretically, a small particle may not sediment in any amount of time at too low a sedimentation force (e.g., colloids). In practice, some bacteria will not sediment at the force of the "clinical centrifuge". Bacterial cell walls or "bacteria fragments" require a higher sedimentation force. Dead or damaged bacteria may have a lower density than viable bacteria. It is important to apply a strong enough force to sediment all bacteria, especially when the difference between the density of the bacteria and that of the medium is minimal. Generally, it has been found that the preferred centrifugal force of from about 4,000 to 11,000 times gravity for from about 10 to 15 minutes is adequate.

Step 3(a)

Removal of sugar, soluble protein, crystals, and excess salts: Step 3 (a) is an optional step utilized where the urine sediment from Step 3 contains substances which may interfere with the retention of bacteria on the slide, with the staining of bacteria or bacterial parts, or with visibility of the bacteria in the sediment. Such interfering substances include soluble salts, glucose, soluble proteins or crystals of uric acid, calcium oxalate, calcium phosphate or the like. The removal of such interfering substances enhances the detection of bacteria and formed elements in the sediment.

Step 3(a) preferably is utilized in the following circumstances:

(1) If the urine contains significant quantities of glucose, or excessive water-soluble salts such as sodium phosphate, or other water soluble substances not removed by the lipid solvent, then the glucose, etc., in the interstices between particles of sediment may interfere with fixation of the bacteria to the slide. The glucose, etc., will redissolve when an aqueous stain is applied and will release the sediment from the slide. Any bacteria not already attached directly to the slide will be lost. Step 3(a) removes these water-soluble substances.

(2) In urine samples containing visible crystals of calcium oxalate, calcium phosphates, urates, etc., which may occlude staining, which may retain stain in its own interstices, or which may obscure or confuse microscopy of the stained specimen, Step 3 (a) is preferred.

(3) Step 3(a) may also be routinely used for parallel or repeat samples should ambiguous or marginal results be obtained using the present process without 3(a).

(4) Similarly, if the urine contains about 30 mg% or more of soluble protein (e.g., albumin, etc.), that soluble protein (1) may not only release any bacteria and formed elements of sediment, but (2) it may also interfere with detection of bacteria after staining because it will fix and stain as a somewhat homogenous mass, or it may occlude the stain from reaching the bacteria. Unlike glucose, most of the soluble protein will be fixed onto the slide when fixatives such as glutaraldehyde and alcian blue are applied. Excessive fixed protein will form a brittle film on the slide. Large portions of this film may break off in the staining procedure. Even then there is a remarkable tendency for the released film to leave behind the formed elements (especially the bacterial parts) which remain fixed to the slide, probably by contacting and adhering to the slide before fixation. That portion of the protein which remains on the slide stains as a homogenous film with a density and color much like the formed elements themselves. During the examination for bacteria using the oil objective (1000x), the stained protein film may obscure bacteria and important formed elements in the sediment, especially Gram negative bacteria and damaged bacteria ("exploded cocci"). Since some of these bacteria are usually still demonstrate inside the protein mass (particularly by special optical means), or seen in the areas of the slide where the protein film has been lost, then the preparation is not completely lost. If a thick protein film adheres, then it may occlude stain from reaching the bacteria, particularly in a rapid staining procedure. Step 3(a) avoids these problems.

(5) Urine sediment may also contain excessive amounts of mucoproteins, such as the Tamm-Horsfall protein, which redissolve without alcian blue or which react with alcian blue to peel off of the slide bearing sediment. When the sediment is deposited with some remaining supernatant, this efflorescence of mucoprotein may release particles in sediment. These mucoproteins are removed by the wash as described.

Step 3(a) is carried out by twice washing the sediment from Step 3 with a sterile, particle-free aqueous solution, preferably slightly hypertonic to normal serum, each wash step being followed by centrifugation.

Specifically, one preferred wash solution comprises an aqueous solution of from about 0.15 to about 0.25 N sodium chloride to which about 0.005 ml of a wetting agent (e.g., Tween 80 or Triton X-100) has been added. The wash solution may be sterilized and rendered particle-free, for example, by passing it through a filter whose pore size is 0.22 microns or less.

It is preferable to add a small quantity of fixative to this wash solution, e.g., 0.5 ml of the methanolic alcian blue fixative and 15 ml glacial acetic acid to 1 liter of 0.2 M NaCl. If a blue sediment appears with standing, it can be filtered or decanted. If the specimens are to be used for fluorescent staining, however, the alcian blue must be omitted in this step because it absorbs the incident ultraviolet light.

Other wash solutions can be and have been used.

In practice, the sediment from the performance of Step 2 is dispersed in about 3 ml of the wash solution and is centrifuged at about 4,000 to 11,000 times gravity for about 5 minutes. The supernatant is removed, and the sediment is again dispersed in about 3 ml of the wash solution and again centrifuged.

The effect of the washing technique of Step 3(a) upon subsequent examination of the wet sediment, upon fixation to a slide, and upon staining as hereafter disclosed are generally as follows:

(1) Under low magnification (100 x) formed elements (e.g., casts, white blood cells, red blood cells, tubular epithelial cells, urothelial cells, bacteria) are more readily seen than in unwashed sediment, particularly if crystals have been removed, and if a small amount of dye (e.g., Light Green, C.I. 42095) is added to the wash solution.

(2) When dried on the slide, the washed sediment adheres very well to the glass through subsequent fixation and staining.

(3) The gross appearance of a Gram-stained slide of washed sediment is somewhat different than that of unwashed sediment. The fixed washed sediment is more dense, and it stains more red instead of blue because some material has been removed in the wash, material such as the glycoproteins (the Tamm-Horsefall protein, etc.) which stain with the alcian blue. Gram staining of bacteria from fresh in-vitro cultures is not altered, but bacteria in urine may be changed, perhaps due to damage in-vivo. Some Gram positive rods in urine will stain Gram negative with or without Gram positive spots or inclusions, and some Gram positive cocci will become Gram negative. Some Gram negative cocci will appear Gram positive because an occluding coating of protein was removed. But, having removed most of the protein (along with glucose, salts, etc.), Gram negative sediment (such as bacteria, "exploded cocci", cells, and casts) previously obscured by being within a similarly staining homogenous protein mass, now stand out.

Step 3(b)

Wet enzyme treatment: Insoluble proteins are removed by incubation with bacterial or fungal proteases or proteolytic enzymes of animal origin, such as crystalline trypsin and chymotrypsin. Fresh urine is centrifuged as in Step 3 at 11,000 × gravity for 10 to 15 minutes. The supernatant is removed, and a particle-free buffered solution of crystalline trypsin or of a bacterial protease is added to the sediment, preferably with a small amount of particle-free sodium azide solution to prohibit bacterial growth. After dispersing the residual sediment, the tube is incubated, preferably at 37° C. for 10 minutes or for a time appropriate for the enzyme at the concentration used. The tube is then centrifuged at about 11,000 × gravity for 5 minutes. The supernatant is removed, and the sediment is washed and centrifuged twice as in the above Step 3(a). Proteolysis by trypsin may be used to remove previously soluble proteins that have been precipitated by the preservative. If not removed, these proteins may interfere with staining and with visualization of bacteria.

This enzyme treatment removes some of the insoluble proteins. Two advantages are noted. First, some of the sediment is removed, but bacteria, degenerated bacteria, bacterial parts, host cells, and casts are usually spared. This provides a means to concentrate important sediment such as bacteria. Second, the staining of some bacteria is changed. Most notable is the ability to detect Gram positive cocci in sediments that contain only Gram negative cocci in their unwashed or washed preparations. Since the Gram positive characteristic is peculiar to the cell wall of these bacteria, it is quite unlikely that proteolytic enzymes would create the conditions for a positive strain (retention of the iodinated crystal violet). Instead, it is likely that such proteolytic enzymes remove a protein from the bacteria, for example an adherent human antibody which had coated the bacterial cell wall and had prevented the gentian violet from penetrating to, or fixing to, the bacteria.

Step 4

Dispersion: Step 4 can be carried out alternately (a) directly from the centrifugation Step 3, or (b) from the wash Step 3(a), or from wet enzyme step 3(b) previously described. After removing the supernatant, the sediment is dispersed in the residual clear fluid (about 0.1 to 0.2 ml. in an ordinary conical centrifuge tube) and the suspension is spread on a clean glass slide. The quantity of this residual liquid and the sediment may be roughly measured by weighing the centrifuge tube with and without the residue, and estimating the specific gravity to be about 1.1. A measured aliquot (0.02 to 0.05 ml.) of the 0.1 ml of sediment can be spread over a 1 or 2 square centimeter area to quantify the bacteria. The slide may now be viewed wet without a cover slip at 100 to 400 ×.

Step 5

Drying: The slide is then dried slowly by any means suitable for conventional preparation of bacterial slides, e.g., at about 40°–50° C. under an airstream (such as an ordinary portable hair dryer).

Step 6

Removal of Lipids or Lipid-Soluble Substances: A key step of the improved process of this embodiment of the present invention comprises removal of lipids of lipid-soluble substances. The lipids found in urine are in the range of polarity (in a thin layer chromatogram) of the naturally occurring phospholipids such as lecithin, but they do not contain significant phosphorus. Like phospholipids (or other substances in that polarity range), they are surface active agents. Preferably they are removed from the dried sediment by a solvent system such as a mixture of absolute methanol and a halogenated hydrocarbon (e.g., 1,1,1,-trichloroethane in absolute methanol at about 30:1 vol/vol ratio) or by methanol alone. In practice, a lipid wash solution is prepared by adding about 15 ml. of 1,1,1-trichloroethane to about 450 ml. of absolute methanol. The sediment is exposed to the lipid solvent system for about 1–30 seconds.

Step 7

Fixation: Results are improved by fixation at this point. A dilute solution of glutaraldehyde in absolute methanol (e.g., 1 ml glutaraldehyde in 450 ml. of absolute methanol) is used as the initial fixative. Following such exposure, it is preferable to further fix the sediment on the slide by exposure to a solution of alcian blue (Merck Index, 10th ed., No. 208) in acidified methanol. In practice, the alcian blue solution is prepared by adding 150 mg. of alcian blue and 4.0 ml. of glacial acetic acid to 100 ml. of absolute methanol. Should the dye precipitate, slightly more acid may be added. The dried urine sediment on the slide is exposed to each fixative for about 1–30 seconds.

Step 7(a)

Enzyme treatment: In an alternate embodiment, a slide, prepared according to the method of FIG. 1, may be treated following step 6 with a proteolytic enzyme, or the slide may be treated with the enzyme after Step 7's fixation with glutaraldehyde and even after fixation with alcian blue. A solution of enzyme in the appropriate buffer is simply applied to the slide. The slide is incubated at room temperature or at 37° C., washed with sterile saline, fixed again with alcian blue and stained. Steps 8 through 10 are then performed as in FIG. 1.

Step 7(b)

UV Fluorescence Staining: Since a heavy deposit of alcian blue will absorb ultraviolet light, this fixative cannot be used for UV fluorescence staining. Step 7 may be modified to permit UV fluorescence staining by either increasing the glutaraldehyde concentration several fold or the duration of exposure to the fixative (e.g., about 5 minutes). Then the slide may be stained with (a) an ultraviolet fluorescing dye (e.g., a stabilized solution of acridine orange, or a solution of a chemical like the antibiotic tetracycline), (b) an antibody (e.g., a fluorescent antibody—preferably monoclonal—to a specific chemical in a particle in the sediment), or any other target specific substance (e.g., an enzyme labeled with a fluorescent dye). Caution: excessive fixation with an aldehyde will result in spurious information from acridine orange. Acridine orange, and most similar cationic dyes, themselves exert a fixative effect.

In still other embodiments, the urine sediment is treated with other enzymes or antibodies to reveal additional information. Enzymes such as trypsin or other proteases will selectively remove proteins and have been found to uncover bacteria in the sediment that had been masked by protein; i.e. protein which has occluded or otherwise prevented the Gram stain from binding to the bacteria. Thus, cocci may be found to be Gram positive after treatment with trypsin. Enzymes may also be used to identify any formed element in microscopy by solubilizing and thus removing the particle. Should a particle be removed by a substrate-specified enzyme, then the nature of the particle is identified (e.g., if a protease dissolves a particle, the particle was a protein). Among the enzymes that may be so employed are amylase (to remove carbohydrate polymers), DNases, RNases, lipases, lecithinases, sphingomyelinases, sialases, neuraminidases, and hyaluronidases. Enzymes may be used to uncover the surface of bacteria so that a specific antibody or enzyme may then bind to that surface. Such antibody or enzyme may be tagged for visualization by binding to it any fluorescent dye, (e.g., fluorescein, lissamine-rhodamine, etc.). Among the polyclonal or monoclonal antibodies which may be utilized are anti-human IgG, IgM, and IgA, to demonstrate the presence of human immunoglobulin or of a chemical on the bacterial surface or on other elements of the sediment. Rinse with water and dry and go to Step 10.

Step 8

Rinse: Preferably the slide from any of steps 7, 7(a) or 7(b) is washed with pure methanol to remove residual alcian blue. Alternately, the solution of methanol/1,1,1-trichloroethane (about 30:1 vol:vol) may be used.

Step 9

Non-fluorescent staining: A conventional non-fluorescent stain, such as the Gram stain, may be used as may a counterstain such as safranin. The Gram stain has the time-honored advantage of being used in the classification of bacteria.

Step 10

The slide is dried and examined, e.g., at 1000 diameters without a coverslip. Special optics (e.g., epi-ultraviolet or phase) may be used.

Figure 1:
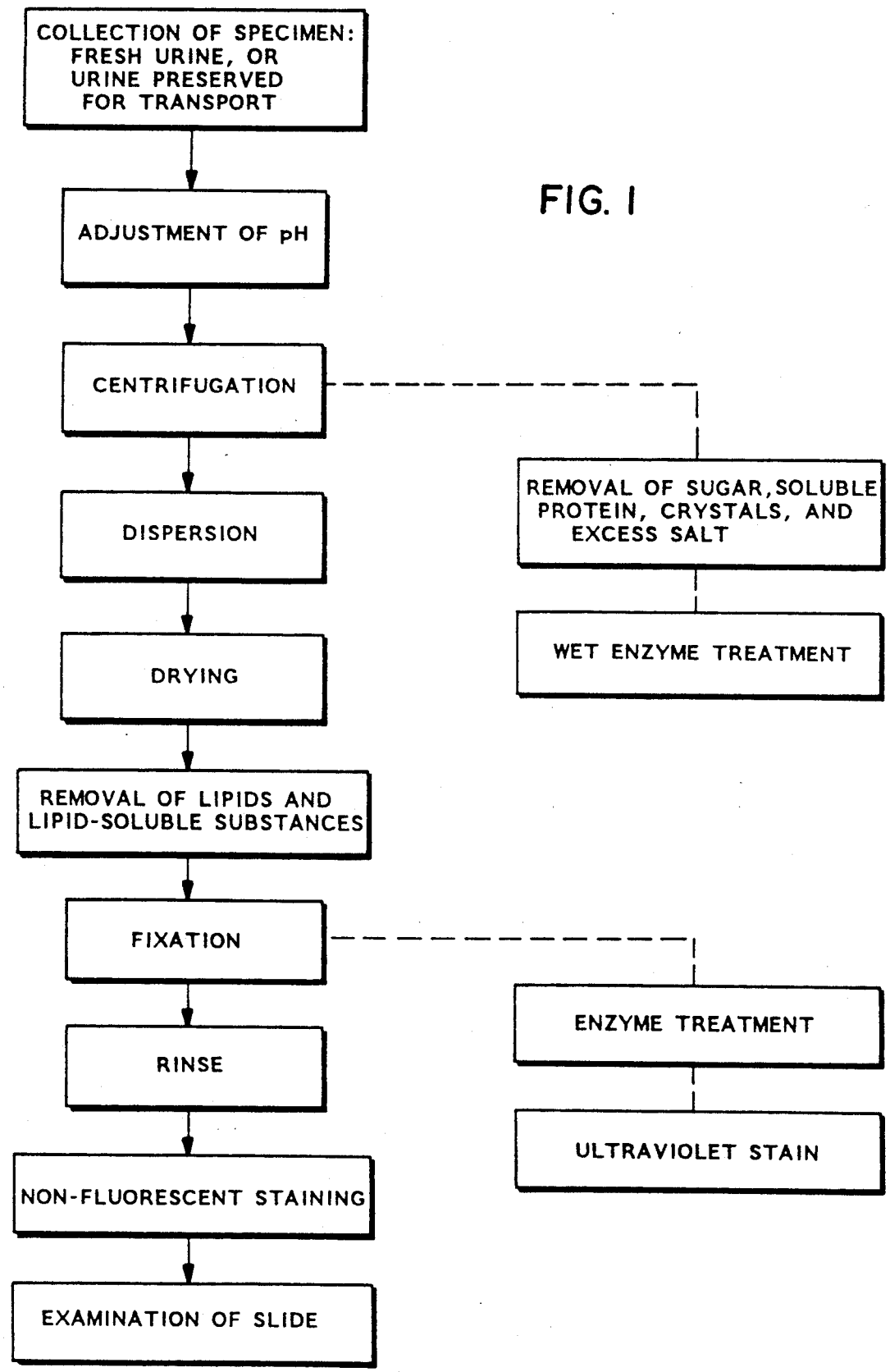
FIG. 1 is a schematic representation of the steps of an improved method for detecting bacteria in urine samples.

Several other optional steps may also be performed in the method of FIG. 1 for detecting bacteria in urine as follows.

Staining of Formed Structures: a wide variety of stains may be added at any step. This includes "vital" stains which penetrate living and dead cells at different rates and which stain intracellular components differentially. For example, brilliant cresyl blue or trypan blue may be used. These dyes enhance visualization of the structure of formed elements of urine (casts, leucocytes, tubular epithelial cells, etc.) as well as the bacteria or bacterial fragments. Although this step enhances microscopic visualization of formed elements and bacteria at 100 diameters magnification, it is usually not essential. The "vital" stain may be applied at any time before steps 2, 3, 3(a) or 4, or in the preservative.

Other positive embodiments of this procedure, not differing in essence from the invention herein disclosed, will be apparent to a person of ordinary skill in the art.

Use of antibodies: According to the present invention, bacteria, bacterial fragments and bacterial antigens demonstrated herein to be associated with rheumatoid arthritis and related diseases, "essential" hypertension, etc., alternatively may be detected in urine samples using antibodies specific for soluble or insoluble antigens produced by such bacteria, these bacteria having been disclosed by this invention. As explained in detail above, such gram positive bacteria include but are not limited to: *Streptococcus faecalis; S. faecium; S. mitis; S. mutanes; S. mutans; S. viridans; S. intermedius; S. salivarius; Staphylococcus epidermidis; Staph. hemolyticus; Staph. hominis; Peptococcus*, etc.

Both conventional polyclonal antibodies (antisera) and monoclonal antibodies can be used. Monoclonal antibodies offer the advantage that large amounts of monoclonal antibody specific for a single bacterial antigen can easily and inexpensively be produced.

Kits employing such antibodies for use in enzyme-linked immunosorbent assays, fluorescence quenching, fluorescence polarization assayes or other methods for the detection of Gram positive bacteria in urine are also encompassed within the scope of the present invention.

Thus, it can be seen that the present invention has several basic advantages over the prior art methods, including:

1. The detection of bacteria (dead or alive, whole or partial) not earlier observed in the urine of patients suffering from the above recited illnesses.

2. The rapid positive identification of both bacteria and bacterial fragments detected and stained by the methods of this invention within a treatment time frame measured in minutes or hours from the time of taking an initial urine sample.

3. The treatment of the various illnesses by the administration of therapeutically effective dosages of antibiotics specific to the illness.

4. The monitoring of treatment by the detection and identification of bacteria in the urine of the patients being treated.

The methods of the present invention to obtain these four basic advantages are characterized by several specific improvements over the prior bacteria detection and identification techniques.

One improvement of the present invention is based on the discovery that urine contains lipids which act as detergents and interfere with adherence of bacteria and bacterial fragments to a slide. Thin layer chromatography of these lipids in a solvent system appropriate for lipids commonly found in human tissues such as phosphatidylcholine (lecithin), phosphatidylethanolamine, phosphatidylserine, and sphingomyelin, reveals that these lipids are in the same range of polarity as human phospholipids. These lipids however, do not contain appreciable phosphorus, and thus they are for the most part not phospholipids. If these lipids are allowed to remain with dried urine sediment on a slide, they will cause the sediment to partially or completely release from the slide when an aqueous solution is applied. The bacteria in the sediment would be lost before they could be seen. This is one reason why past methods of direct microscopy have failed to detect significant members of bacteria in the urine of patients with diseases such as rheumatoid arthritis, etc., and one reason why the teaching with regard to these diseases has been that significant bacteria are not present in the urine. Standard methods of preparing and staining urine specimens for microscopic examination do not provide for the precautionary removal of these lipids.

Another improvement of this invention involves the further fixation of bacteria and other urinary sediment onto a glass slide. Whereas delipidation of the dried sediment improves adherence of bacteria to a glass slide, much stronger adherence is obtained by the use of certain chemicals which do not interfere with the staining of the adherent sediment. This includes fixation of proteins of the sediment with glutaraldehyde and the fixation of glycoproteins of the sediment with alcian blue.

Another improvement involves the removal of crystals and of excesses of water soluble releasing agents such as glucose and soluble proteins by washing the urine sediment.

The positive identification of the various types and states of bacteria (i.e., live bacteria, dead bacterial and bacterial fragments) is also an improvement of this invention. Only live bacteria (and usually non-fastidious) can be detected and identified by the present conventional cultural methods. Culture methods for fastidious bacteria and usually too cumbersome and too expensive for routine use. Dead or fragmented bacteria simply will not grow in any of the culture media.

Yet the presence of the previously undetected dead or fragmented bacteria is highly relevant to diagnosis and treatment by the present invention. If dead or fragmented bacteria are present in the urine, these bacteria were once alive and came from a source within the patient. Cessation of the excretion of both live and dead bacteria in urine of a patient, whose urine had contained these bacteria or bacterial parts, is evidence that the source of live bacteria has been eradicated or sealed off (even if not permanently), and suggests that the patient has been adequately treated for that time. (N.B. Recurrence of bacteriuria after treatment suggests that the bacteria are "protected" in some locus within the body of the host, or it suggests reinfection).

The non-cultural methods of the present invention result in a rapid, yet positive detection and identification of bacteria and bacterial fragments within a time span to accomplish treatment during the same day or even during the same office visit, as opposed to the 3 to 6 days required for culture growth and analysis. The advantages to the practitioner and to the patient are obvious.

The treatment aspect of the present invention is undertaken only after detection and identification of the bacteria (alive or dead, whole or fragmented) has been completed. Thus, a proper antibiotic to be administered and the proper dosage is predetermined from the prior analysis.

The monitoring of the treatment by the same detection and identification method ensures the eradication of bacteria (live or dead, whole or fragmented) from urine excreted prior to cessation of treatment. It also may indicate the desirability of a change in the treatment, either in the specific antibiotic, the use of a supplemental antibiotic or a variance in the dosage level.

Association of Bacteriuria with Various Diseases

By this invention microscopic bacteriuria has been found in persons with a wide variety of illnesses most of which are currently thought to be unrelated to any disorder of the urinary tract and thought to be unrelated to each other. However, disregarding the organ involved, at the microscopic level or at the molecular level there is significant similarity between these illnesses. In the past, a bacteriologic etiology has been entertained as a cause of many of these illnesses only to be abandoned because the bacteria sought, or their "fingerprints", could not be found. In the work that led to this invention the bacteria were found first, and the associated illnesses were found by examination of the urines of every patient irrespective of the disorder. A cause-and-effect relationship was then found not by the classic Koch's postulates, but instead by giving the appropriate antibacterial agent to eliminate the bacteriuria, and then witnessing improvement or remission of the illness as a result of giving an agent whose only known benefit is in eliminating bacteria. Thus the bacteriuria was related to the causation of the illness, and pragmatically, the patient benefited. Except in the obvious instances such as pyelonephritis (which literally means inflammation of the kidney with pus), the finding of bacteriuria does not mean or infer that the bacteria had colonized the kidney. They may have been simply "cleared" from the blood by the kidney and excreted in the urine, perhaps being carried within a phagocyte. For the above reasons, it appears that the finding of microscopic bacteriuria is evidence of a disease process and not a disease. In each of the clinical illnesses to follow a causal relationship is strongly supported by having witnessed clinical improvement induced by the antibiotic. In a few instances so stated, or marked by an *, bacteriuria was found, but there was no follow-up with appropriate antibiotics, and therefore a causal relationship can only be inferred.

By this invention, the diseases found causally related to microscopic bacteriuria include osteoarthritis, rheumatoid arthritis, and related syndromes such as juvenile rheumatoid arthritis, ankylosing spondylitis, Reiter's disease, palindromic rheumatism, myositis, fibrositis, bursitis, tendonitis, tenosynovitis, the carpal-tunnel syndrome, panniculitis, tempero-mandibular arthritis, sacroiliac arthritis, systemic lupus erythematosis, erythema nodosum, scleroderma, isolated Raynaud's phenomenon, and other rheumatic diseases. Microscopic (coccal) bacteriuria has been associated with rheumatic heart disease, even when there has been no cultural or serologic evidence of the culpable group A beta-hemolytic streptococcus, but there was evidence of smoldering activity of the rheumatic process. It has been found in patients with hypertension, with presumed idiopathic myocarditis, and with mitral valve prolapse, with or without evidence of "microembolism". Microscopic bacteriuria has been causally associated with various forms of inflammatory bowel disease including Crohn's disease and ulcerative colitis. It is associated with classic migraine and with other kinds of headache, and with Meniere's syndrome. It has been found in various forms of vasculitis, not only the vasculitis of rheumatoid arthritis, but also in retinal arteritis and temporal arteritis; and without followup, in Takayasu's disease and Kawasaki's disease. Without strong evidence of a causal relationship, it has also been found in a patient with a dissecting aortic aneurysm, and with the "subclavian steal" syndrome (clotting of a segment of the subclavian artery due unknown cause. The segment is thought to become inflamed first.)

In renal diseases microscopic (coccal) bacteriuria occurs in recurrent classic pyelonephritis (as suggested by H. C. Bumpus and J. G. Meisser, Archives of Internal Medicine, vol. 27, pp. 326–337, 1921), and remains after elimination of the usual Gram negative rod-shaped bacteria; and elimination of the cocci found has resulted in cessation of recurrences Microscopic bacteriuria is found associated with the progressive loss of renal function in clinical pyelonephritis when the "infection" is supposed to have been eliminated (see also M. E. Angell, A. S. Relman, and S. L. Robbins, "Active" Chronic Pyelonephritis without Evidence of Bacterial Infection, New England Journal of Medicine, vol. 278, pp. 1304–1308, 1968). Similarly it is present in unexplained renal failure, and in renal failure due to polycystic kidneys in adults, and reversal of the renal failure has occurred with relief of the microscopic bacteriuria. It occurs with kidney stones and elimination of the bacteriuria has resulted in cessation of stone formation; and with cystitis, whether or not the urine is "sterile" on routine culture. Microscopic bacteriuria was found in a proven case of "interstitial cystitis", but treatment was not possible. Elimination of microscopic bacteriuria has resulted in improvement or even remissions in the nephrotic syndrome in adults and in children; and improvement in glomerulonephritis, in "chronic nephritis" or interstitial nephritis thought to be sterile but progressive. It occurs with otherwise unexplained proteinuria, and many of those patients have been benefited by elimination of the bacteriuria. Microscopic bacteriuria is found in persons with unexplained edema(salt retention), and in classic chronic lymphedema of the legs (e.g., "milk leg"), and those patients are greatly benefited.

Elimination of microscopic bacteriuria has also resulted in a remission in a patient suffering from proven retroperitoneal lymphadenitis and in others with unexplained deep abdominal pain that could be due to that disease. Similar results have been had in patients with the symptomatology attributed to a "hiatus hernia". It has been found associated with a crisis in sickle cell anemia* . Isolated iritis or uveitis has been relieved by relief of the concurrent bacteriuria. Patients with associated lung disorders such as status asthmaticus, chronic obstructive pulmonary disease (COPD), and just subjective dyspnea without COPD have benefited.

Elimination of concurrent bacteriuria has resulted in improvement or remission of a vast array of vague disorders, many of which have been defined recently as the Chronic Fatigue Syndrome (see G. P. Holmes, J. E. Kaplan, N. M. Gantz et al., Chronic Fatigue Syndrome: A Working Case Definition, Annals of Internal Medicine, volume 108, pages 387-389, 1988.). These include loss of stamina, sleep disorders, loss of memory, etc.; and it also includes nocturnal leg cramps ("charley horses"), easy bruising, and unexplained chills and sweats. Relief of bacteriuria has resulted in elimination of the symptoms attributed to a "Thoracic Outlet Syndrome" and to "Transient Ischemic Attacks" or "Little Strokes"; and elimination of bacteriuria has relieved the periodic fainting and other symptoms attributed to an idiopathic "autonomic disturbance". Microscopic bacteriuria, often with some of the above vague symptoms, may appear to stay after splenectomy. It has been observed to follow an automobile accident in which there is blunt trauma to the abdomen, or a long vehicle ride in which there is prolonged vibration affecting the abdomen. Perhaps, under these circumstances, bacteria get through the thin intestinal lining into the lymphatics and thereby to the kidney. Like the well established appearance of viable bacteria in the blood after dental work, an abscess at the root of a tooth, or sinusitis, bacteriuria is also found. Perhaps this bacteriuria results from the known bacteremia.

Treatment of patients suffering from the above-mentioned diseases or conditions, using appropriate antibacterial agents, has resulted in improvement or resolution of the clinical manifestations of the illness along with elimination of bacteriuria. Thus, it appears that these diverse diseases may, at least in part, be manifestations of the same or of similar bacterial invasions or that the given disease is aggravated by the bacteria seen. The diversity may simply reflect varied responses of a human host to such invasions. It is believed that many of these diseases reflect varied host responses to the bacteria themselves, to bacterial components, to bacterial antigens, or to antigenic substances produced by such bacteria. Perhaps the differences in host response are in part inherited traits.

According to the present invention, bacteria, dead or alive, detected in urine do not necessarily represent active bacterial infections (colonization) of the urinary tract. Rather it is currently thought that the majority of presently detected bacteria originate from sites of bacterial infections or infestations of other parts of the body, and that the bacteria or bacterial parts are excreted by the kidney.

In a number of instances, bacteria have been observed sequestered in neutrophils or machrophages voided from the body in the urine. It is postulated that the dead bacteria and "exploded" cocci observed in the urine specimens may have been previously sequestered in neutrophils or macrophages that have been released into the urine and eliminated from the body. The present invention, however, is not to be limited to this or any other mode by which the bacteria may have been introduced into the urine by the kidney.

Using the methods of this invention, as above described, bacteria and bacterial fragments, often in fairly large numbers, have been observed in urine samples from patients hospitalized for treatment of the above-listed diseases and conditions. Results are illustrated in Table II.

As demonstrated in Table II, the majority of urine samples observed contained significant numbers of small (perhaps growth-stunted) Gram positive cocci, usually in pairs, i.e., diplococci.

TABLE II

In Table II, a number in the first column following the patient identification indicates replicate urine samples.
The following abbreviations are used to describe bacteria and formed elements observed under a microscope at 1000 × magnification (oil immersion lens) in dried and stained preparations of urinary sediment prepared according to the methods heretofore described herein.

| | |
|---|---|
| Gm+ | Gram positive |
| Gm− | Gram negative |
| Gm+/− | mixed Gram positive and Gram negative |
| Coccus | spherical or nearly spherical bacterium occurring singly |
| Expl. Coccus | "exploded" coccus; dead coccus without nucleic acids which resemble published electron photomicrographs of Staphylococci or Streptococci whose cell walls had been ruptured by natural host defenses, by antibiotics, or by chemical or mechanical means. These "exploded cocci" appear in the stain just like the cell walls of staphylococci or streptococci that have been isolated by mechanical means in from intact cocci grown in laboratory culture. Thus the finding in urine probably .pa represents cell walls of exploded bacteria. This conclusion has been supported by chemical analysis. |
| Diplo. | diplococcus; cocci in pairs. |
| Staph. | Staphylococci, or Gram positive cocci which tend to group in clusters |
| RBC | red blood cells or erythrocytes. |
| WBC | white blood cells or leucocytes (polymorphonuclear leucocytes, lymphocytes, monocytes, etc.) |
| Micrococcus | small Gram positive coccus, usually grouped with Staphylococci. |
| Encap. | Encapsulated bacteria. |
| Strepto. | streptococci, cocci that tend to form a chain like a string of beads. |
| Degen. | degenerated or fragmented (cocci). The term is used to describe cocci whose margins are not as indistinct as those of exploded cocci; some may be viable. |
| 1+ | estimate of quantity of bacteria or element seen on a scale of 0–4. A single plus usually means 1–2 per oil field. |
| 2+ | 2–8 per oil field. |
| 3+ | 15–40 per oil field. |
| 4+ | the bacteria are maximal nearly forming a complete covering of the slide |
| Round Cells | Rounded or elliptical cells sometimes over 35 μm in their larger diameter. Many may be "urothelial" cells, but certainly some are macrophages. For a lack of a rapid method of designation, they are simply referred to as round cells. |

TABLE II-continued

| | |
|---|---|
| Granular Protein | Protein or protein containing material which dries on a slide in a granular pattern, suggesting that the material is derived from structural material of cocci and dries in a granular pattern, i.e., suggestive of severely degraded cocci. |

RESULTS OF MICROSCOPIC EVALUATION OF URINARY SEDIMENT FROM PATIENTS WITH ENUMERATED DISEASES AND USING IMPROVED METHODS OF PRESENT INVENTION

| PATIENT | BACTERIA | FORMED ELEMENTS OBSERVED |
|---|---|---|
| HW | Expl. cocci 3+<br>Gm+ Staph. | Coarse Granular casts |
| PA | Expl. cocci 1+ | Protein 1+;<br>RBC/WBC 1+ |
| KK | Gm+ Diplo. rare<br>Expl. cocci 2+<br>Diphtheroids 1+ | |
| MAT | Gm+ Diplo. 1+<br>Diphtheroids 1+ | |
| RG | Encap. Gm+ Diplo. 1+<br>Diphtheroids 1+ | |
| RO | Expl. cocci 2+ | Protein 2+ |
| JA2 | Encap. Gm+ Strepto. 1+<br>Yeast less than 1+ | |
| SB | Small Gm+ Diplo. 2+ | |
| NB | Gm+/− Diplo. 2+ | |
| JA3 | Expl. cocci 3+ | |
| GD | Gm+ Diplo. 2+ | few casts, round cells, WBC |
| FG | Gm+ Diplo. 1+<br>Expl. cocci 1+ | |
| DM | Gm− rods 5+<br>Gm+ Diplo. 1+ | WBC 3<br>(classic pyelonephritis) |
| KM | Not Available | |
| VH | Gm+ Diplo. 2+<br>Expl. cocci 2+<br>Yeast 1+ | |
| FT | Gm+ Diplo. 1+<br>Expl. cocci 1+ | |
| JH | Gm+ Diplo. 1+<br>Expl. cocci 4+ | |
| DD | Gm+ Diplo. 1+<br>Expl. cocci 2+ | |
| AS | Gm+ Diplo. 1+<br>Expl. cocci 1+ | |
| ET | Gm+ Diplo. 2+<br>Strep.<br>Diphtheroids 1+ | |
| MS | Gm+ Diplo. 1+<br>Gm+ rods 1+<br>Gm− rods 1+ | |
| JF | Gm+ cocci only in casts | Casts 1+ |
| PA2 | Gm+/− cocci<br>Expl. cocci 1+ | |
| RB | Gm+/− cocci 1+<br>Expl. cocci 2+ | Fine Granular casts 1+<br>Insoluble Protein |
| BS | Degen. cocci 2+ | WBC 2+,<br>Ca Oxalate crystals<br>Granular Protein |
| DH | Gm+ Diplo. 2+ | |
| MB | Small Gm+ Diplo. | |
| BB | Gm+ Strepto. | |
| DB | Gm+/− cocci 1+<br>Diphtheroids 1+ | |
| MRM | Small Gm+ Diplo. 1+ | |
| ZP | Gm+ cocci 2+ | WBC 2+ |
| JD | Gm+ cocci 1+;<br>cocci in casts | Coarse granular casts |
| MB2 | Small Gm+ Diplo. | |
| JL | Gm+ Diplo. 1+<br>Expl. cocci 3+ | |
| JH | Gm+/− cocci 2+ | |
| ML | Small Diplo. 2+<br>Gm+ Stepto. 1+<br>Tiny Gm− rods 4+ | |
| GC2 | Gm+ Strepto. 3+ | |
| CB | Gm+/− cocci/Diplo. 3+ | |
| EN | Gm+ Diplo. | |
| JC | Diphtheroids 1+<br>Gm+ Diplo. in clumps 1+<br>Gm+ Diplo. 1+ | |
| CDM | Gm+/− Diplo. or small rods | |
| LS | Gm+ Diplo. 1+<br>Expl. cocci 1+ | |
| MP | Gm+ Diplo. 2+ | |
| LW | Small Gm+ Diplo. 4+ | |
| JB | Gm+ Diplo. 1+<br>Expl. cocci 4+ | |
| KJ | Gm+ cocci 2+<br>Staph. | WBC 2+ |
| AH | Gm+ Diplo. 2+<br>Expl. cocci 1+ | |
| RO2 | Intracellular Gm+ cocci 1+<br>Expl. cocci 3+ | Degen. WBC |
| AP | Gm+ Stepto. 1+<br>Gm+ Diplo.<br>Expl. cocci 2+ | |
| ME | Gm+ cocci in clumps 3+<br>Gm− cocci in clumps | |
| VH2 | Gm+ Diplo. 1+<br>Degen. cocci 4+<br>Gm+ rods 1+ | |
| DW | Gm+ coccus, rare<br>Degen. cocci 1+<br>Expl. cocci 2+ | |
| MS | Not available | |
| BE | Not available | |
| MJK | Gm+ probable small Diplo. | |
| WM | Small Gm+ Diplo. 1+<br>Large Gm+ Diplo. 1+ | |
| JJ | Expl. cocci 2+ | |
| MP | Gm+/− Diplo. in clumps<br>cocci 3+ | Round cells |
| JS | Tiny Gm+ Diplo. 4+ | |
| JH2 | Gm+ cocci 1+ in a cast<br>Gm+ Diplo. | |
| MP2 | Gm+/− Diplo. in clumps<br>Cocci 3+<br>Gm+ Diplo. | Round cells |
| GM | Expl. cocci 3+ | |
| CM | Micrococci 2+<br>Diphtheroids 1+ | |
| SF | Gm+ Diplo. 3+ | |

Small Gram positive cocci were observed in urine specimens of patients suffering from rheumatoid arthritis, rheumatic fever, systemic lupus erythematosis, migraine and other headaches, mitral valve prolapse, renal failure, and other diseases.

Larger Gram positive cocci (often Staphylococci) were often observed in the urine of patients suffering from hypertension, transient ischemic attacks of the central nervous system, and in the few cases seen, IgG nephropathy.

"Damaged" or "exploded" cocci are seen in the company of either large or small Gram positive cocci. Experimentally these forms can be simulated by performing the same staining method on a smear of broken cell walls of staphylococci or streptococci grown in a culture. "Exploded" cocci are thought to be the cell walls of cocci whose contents have been lost when the cell wall (a shell) was opened by host defenses or by previously administered drugs.

The method of the present invention has demonstrated a much higher incidence of bacteriuria in hypertensives, perhaps as high as 90%, as compared to that seen with conventional methods for detecting bacteriuria, i.e., 2–5%. It can be readily shown by staining and microscopy that many of the bacterial forms observed under the microscope using methods of the present invention were not alive at the time the specimen was obtained. For example, some do not contain any nucleic acid, either DNA or RNA, two biochemical components essential to life. Should all of the bacteria in a given specimen be devoid of nucleic acid, then none will grown and the culture of urine is sterile. Indeed the vast majority urine specimens from sick patients containing huge numbers of bacteria as demonstrated by the novel methods of the present invention did not yield a positive culture in the hospital bacteriology laboratory. When the laboratory reports "no growth" the clinician usually abandons the possibility of significant bacteriuria, and hence sets aside the possibility of a bacterial cause, or an infectious element in the patient's illness. Nonetheless, though they do not grow in routine culture, these dead, damaged or fastidious bacteria are or were once alive, and as shown herein, they have caused or exacerbated the illness. They can now be used to diagnose the status of a patient's illness.

Urine samples obtained from the hospitalized patients listed below in Table II were initially cultured under conditions favoring the growth in fastidious facultative anaerobic microorganisms. These conditions include culture at 37° C. in tryptic soy broth and on blood agar plates placed in an anaerobic chamber containing hydrogen and carbon dioxide. Beta phenyl ethanol was added to at least one medium whenever Gram negative rod-shaped bacteria were also seen in the urine or in a culture medium. Results are illustrated in Table III. The definitions and replicates in Table III are the same as in Table II.

TABLE III

ORGANISMS CULTURED ANAEROBICALLY FROM URINE SAMPLE

| PA-TIENT | ISOLATE 1 | ISOLATE 2 | ISOLATES 3/4 |
| --- | --- | --- | --- |
| JC | enterococcus | | |
| JA | Strep. faecalis | | |
| JD | Strep. faecalis | Gm— species | |
| GC | E. coli | | |
| HW | Staph. epidermidis | | |
| PA | Staph., 2 species | | |
| KK | Strep. salivarius | | |
| MAT | Strep. faecalis | | |
| RG | Strep. faecalis | E.coli | |
| RO | Strep. faecalis | E. coli | |
| JA | Strep. faecalis | E. coli | Torulopsis |
| SB | Staph. epidermidis | E. coli | |
| NB | Strep. faecalis | Proteus mirabilis | |
| JA | Klebsiella pneumoniae | Enterobacter sp. | |
| GD | Strep. faecalis | Proteus mirabilis | |
| FG | enterococcus | | |
| DM | enterococcus | | |
| KM | Strep. intermedius | E. coli | |
| BH | enterococcus | Strep. intermedius | |
| FT | Staph. epidermidis | | |
| JH | Strep. mutans | Staph. epidermidis | |
| DD | Staph. epidermidis | Diphtheroids | |
| AS | Strep. mutans | Strep. sanguis | |
| ET | Strep. agalactiae | | |
| MS | Strep. faecalis | | |
| JF | Staph. epidermidis | | |
| PA | Strep. mitis | | |
| RB | Strep. faecalis | Group B Strep. | |
| BS | Staph. hominis | | |
| DH | Strep. viridans | | |
| MB | Peptococcus | Diphtheroids | |
| BB | Strep. faecalis | E. coli | |
| DB | Strep. faecalis | Group B Strep. | |
| MRM | enterococcus | +/— Staph. hominis | |
| ZP | Group D strep. | E. coli | Klebsiella pneumoniae |
| JD | enterococcus | | |

TABLE III-continued

ORGANISMS CULTURED ANAEROBICALLY FROM URINE SAMPLE

| PA-TIENT | ISOLATE 1 | ISOLATE 2 | ISOLATES 3/4 |
| --- | --- | --- | --- |
| MB | Group D strep. | | |
| JL | Strep. mitis | Staph. hominis | |
| JH | Strep. aginosus | E. coli | |
| ML | Strep. faecium | E. coli | Klebsiella pneumoniae |
| AT | Strep. faecalis | | |
| GC2 | Strep. faecalis | Staph. hominis | E. coli/ Klebs. pneumoniae |
| CB | Strep. mitis | E. coli | |
| EN | Strep. mitis | | |
| JC | Strep. faecium | Strep. viridans | E. coli |
| CDM | Strep. viridans | E. coli | |
| LS | Strep. viridans | E. coli | |
| MP | Group D strep. | Proteus mirabilis | |
| LW | Strep. faecalis | Strep. intermedius | E. coli |
| CDM2 | Strep. viridans | Staph. epidermidis | |
| JB | Group B Strep. | | |
| KJ | Strep. faecalis | | |
| AH | enterococcus | Staph. hominis | Staph. haemolyticus |
| SZ | Strep. intermedius | Staph. haemolyticus | |
| RO | Group D strep. | E. coli | |
| AP | Staph. haemolyticus | | |
| ME | Group B Strep. | Staph. epidermidis | |
| VH2 | Strep. faecalis | Salmonella species | |
| DW | Staph. haemolyticus | | |
| MS | Klebsiella pneumoniae | | |
| BE | Strep. faecium | | |
| MJK | Cannot be evaluated | | |
| WM | Strep. faecalis | E. coli | |
| WM | Strep. faecalis | E. coli | |
| MP | Strep. intermedius | Staph. epidermidis | |
| JS | Staph. epidermidis | | |
| JH | Strep. intermedius | Staph. epidermidis | |
| JJ2 | Strep. faecalis | E. coli | |
| MP | Strep. intermedius | Staph. epidermidis | |
| FB | Staph. epidermidis | | |
| CM | Strep. faecalis | | |
| SF | Cannot be evaluated | | |

As demonstrated in Table III, Gram positive cocci were recovered from 67 out of 70 samples cultured under such conditions. The most frequently cultured Gram positive organisms include: S. faecalis; Enterococcus; Staph. epidermidis; S. viridans; S. mitis, etc.

The only Gram negative organisms recovered included: E. coli; Klebsiella pneumoniae and Enterobacter.

Urine samples from a number of the hospitalized patients listed in Tables II and III were cultured by a hospital bacteriology laboratory using conventional urine culture techniques. Results are illustrated in Table IV. ("--" indicates culture was not performed in the hospital laboratory.)

TABLE IV

ORGANISMS CULTURED FROM URINE SAMPLES USING CONVENTIONAL TECHNIQUES

| PATIENT | ISOLATE |
| --- | --- |
| JC | — |
| JA | No Growth |
| JD | No Growth |
| GC | — |
| HW | — |
| PA | — |
| KK | No Growth |
| MAT | No Growth |
| RG | — |

TABLE IV-continued
ORGANISMS CULTURED FROM URINE SAMPLES USING CONVENTIONAL TECHNIQUES

| PATIENT | ISOLATE |
|---|---|
| RO | — |
| JA2 | — |
| SB | No Growth |
| NB | — |
| JA3 | — |
| GD | — |
| FG | No Growth |
| DM | E. coli, 2 species |
| KM | — |
| BH | — |
| FT | No Growth |
| JH | No Growth |
| DD | — |
| AS | — |
| ET | — |
| MS | — |
| JF | No Growth |
| PA2 | — |
| RB | No Growth |
| BS | No Growth |
| DH | — |
| MB | — |
| BB | — |
| DB | — |
| MRM | — |
| ZP | — |
| JD | — |
| MB2 | No Growth |
| JL | — |
| JH | — |
| ML | No Growth |
| AT | No Growth |
| GC2 | — |
| CB | — |
| EN | No Growth |
| JC | — |
| CDM | — |
| LS | No Growth |
| MP | — |
| LW | — |
| CDM2 | — |
| JB | No Growth |
| KJ | Staph. epidermidis |
| AH | — |
| SZ | No Growth |
| RO2 | No Growth |
| AP | — |
| ME | — |
| BH2 | No Growth |
| DW | — |
| MS | — |
| BE | — |
| MJK | — |
| WM | — |
| MP | — |
| JS | — |
| JH2 | No Growth |
| JJ2 | — |
| MP2 | — |
| FB | No Growth |
| CM | — |
| SF | — |

As demonstrated in Table IV, positive cultures were observed in only two of 28 urine samples cultured using conventional techniques. Of the positive cultures, two strains of E. coli and one strain of Staph. epidermidis were isolated. The E. coli grow out from a urine containing Gram positive cocci as well as the rods. Twenty-seven of the twenty-eight tested failed to demonstrate positive cocci in culture despite the presence of Gram positive organisms as demonstrated by the microscopic methods of the present invention and confirmed by culture under conditions favoring the growth of fastidious facultative anaerobic microorganisms. This experience continues to date.

Thus, despite the inability to detect bacteriuria using conventional techniques, detection of bacteria in urine using microscopic examination as described herein is positively correlated with culture of microorganisms under conditions favoring growth of facultative anaerobes.

Moreover, a positive correlation between the microscopic evidence of bacteriuria by the present invention and the therapeutic result upon reduction or elimination of bacteriuria with antibiotics is presented in Table V.

TABLE V
EFFECTS OF ANTIBIOTIC TREATMENT IN HOSPITALIZED PATIENTS
Microscopic Evaluation of Urine

| Patient | Diagnosis | Pre-Treatment | Post-Treatment |
|---|---|---|---|
| SB | Probable RA | Diplo. 2+; Expl. cocci 1+ | occasional cocci |
| EN[1] | Classical RA | Diplo. 1+; Diphtheroids | Expl. cocci 1+ |
| BP[2] | Probable RA | Gm+ Diplo. 1+ | Expl. cocci 1+ |
| GC[3] | Classical RA | small Strep. 4+ | Gm− Rods with thick capsules 1+ |
| ET[4] | Definite RA | Expl. cocci 3+/4+ Gm+ Diphtheroids with chains | rare Gm+ Strep. |
| CS | Definite RA | Expl. cocci 3+ | occasional Expl. cocci Gm− rods 1+ Occasional WBC |
| RB[5] | Classical RA | Expl. cocci 2+ Gm− cocci 1+ fine gran. casts | Negative |
| JF | Definite RA | Gm+ Diplo. | Negative |
| CLaF[6] | Severe Classic RA | Strepto. 4+ on epithelial cells | Negative |
| EJH[7] | Classic RA | Strepto. 1+ Gm+ Diplo. 1+ | rare Gm− rod Expl. cocci 1+ |
| FG | Probable RA | Gm+ Diplo. 1+ Expl. cocci 2+ | Expl. cocci Expl. cocci 1+ |
| MC[8] | Definite RA | Gm− rods 2+ Gm+ Diplo. 1+ Intracellular cocci 1+ | Gm+/− cocci on epithelial cells |
| HB[9] | Probable RA | Strep. large number Hyaline/ cellular casts Tubular cells | Negative |
| DM[10] | Probable RA | Gm− rods 5+ Gm+ Diplo. 1+ | Negative |
| AS | Reiter's Disease | Gm+ diplo 1+ Gm− Diplo. 1+ Expl. cocci 2+ | few Expl. cocci |
| JH[11] | Ankylosing Spondylitis | Gm+ cocci 1+ Expl. cocci 4+ | Negative |

For detailed explanation of Microscopic Evaluation of Urine, see Table II. All patients were treated with: 1.2–3.0 gm per day of clindamycin and 0.16 gm per day tobramycin administered intravenously, except as indicated below:

| Superscript Number | Departures from Standard Treatment |
|---|---|
| 1 | Plus 2.0 gm per day ceftizoxime |
| 2 | Plus 6.0 gm per day Pipracillin and 0.5 gm cyclophosphamide |
| 3 | Plus 1.0 gm per day cefamandole and intra-articular triamcinolone hexacetonide into one shoulder |
| 4 | No tobramycin; plus 2 gm per day ceftizoxime |
| 5 | No tobramycin; plus 2 gm per day cefazolin |
| 6 | No tobramycin; plus 2 gm per day nafcillin and 1 gm per day amikacin |
| 7 | Plus 1 gm per day cefazolin |

-continued

| Superscript Number | Departures from Standard Treatment |
|---|---|
| 8 | No tobramycin; plus 2.0 gm per day amoxacillin and 500 mg per day potassium clavulanate: and 1.0 gm per day tetracycline by mouth |
| 9 | Plus 1 gm per day tetracycline by mouth |
| 10 | Plus 6.0 gm per day ticarcillin |
| 11 | Plus 6.0 gm per day ticarcillin |

As demonstrated in Table V, in all patients examined suffering from either probable, definite or classic rheumatoid arthritis, microscopic examination of urinary sediment before and following treatment with antibiotics showed significant reduction or even resolution of bacteriuria following treatment. In six out of sixteen patients, post-treatment urine samples were essentially free from bacteria. All patients included in Table V showed simultaneous significant improvement if not elimination of clinical symptoms of rheumatoid arthritis.

To quantify the number of bacteria or bacterial fragments, the following technique was devised.

Thirteen ml. of urine in a sterile graduated 15 ml conical centrifuge tube was centrifuged at $4000 \times g$ for 10 minutes. The supernatant was decanted, and the residual fluid drained back onto the sediment at the bottom of the tube. The volume of sediment plus residual fluid was read from the calibration. It was usually between 0.1–0.14 ml. The sediment was resuspended in the fluid. Using a sterile micropipette, 0.01 ml of sediment was spread evenly on a marked 1 or 2 square centimeter area of a clean glass slide. The field of the microscope is calibrated by viewing a stage micrometer (a slide with rulings at 0.01 mm) at the 1000 diameters magnification used to view bacteria. For example, if the diameter of the field of view in a microscope is 0.0183 cm, there are 3,800 such fields per square centimeter of slide. Alternatively, the field may be photographed. For exaMple, in a photographic tube of the microscope, the rectangular marking used to delineate a 35 mm camera field measures $0.0038 \times 0.0026$ cm. There are 101,000 such fields per square centimeter of the slide. Alternatively, a reticule for the ocular of the microscope may be used which superimposes a square onto the visual field. Using the 1000 diameter optics, this square is 0.0071 cm on a slide, and there are 19,600 such areas per square centimeter of the slide. The reticule is divided into 100 squares for easy counting of the overall square.

Using any of the above, the average number of the bacteria of numerous samples was determined. Since the area of the smear is known, and the quantity of urine represented per 1 or 2 square centimeters is also known, then the number of each kind of bacteria is obtained by simple multiplication. The remainder of the sediment is used for a count by culture. It is washed into 4 ml of a rich broth (e.g., trypticase soy broth) and put through serial dilutions to lower the count. One ml aliquots of each dilution are layered onto each of two Blood Agar Plates (BAP). One is incubated aerobically and one anaerobically (in a BBL Laboratories "GasPak", a jar with hydrogen gas and a palladium catalyst to achieve true anaerobic conditions, i.e., an extremely low oxygen pressure, and a very low oxidation potential). If, in the smear, there is any contamination by Gram negative rods a BAP plate containing 2-phenyl-ethanol may be used to inhibit the rods. The count by culture is done after a good growth is achieved. This may take one week. Most hospital laboratories discard the culture in 48 hours because the Gram negative rods most frequently found usually grow in that time. If the cocci do not grow in that 48 hours, they will never be detected by that culture technique, and they will never become the usual organisms found. Many cocci and Gram positive rods take longer. Counting and multiplying by the dilution is a routine procedure. Results are illustrated in Table VI.

TABLE VI

| QUANTIFICATION OF BACTERIA AND BACTERIAL FRAGMENTS OBSERVED | | | |
|---|---|---|---|
| Patient/Diagnosis | Microscopic Evaluation Bacteria per ml. | Culture Colonies/ml. | Routine Hospital Culture |
| DJ/probable RA | $2.65 \times 10^6$ Large Gm+ cocci | $6.3 \times 10^6$ | $10^3 - 5 \times 10^4$ |
| MB/RA | $1.7 \times 10^4$ Large cocci | $3.2 \times 10^2$ (anaerobic staph) | Negative |
| MB2/RA | $1.0 \times 10^4$ Small cocci 113 Staph $6.3 \times 10^6$ Expl. cocci | 3 | Negative (On antibiotics) |
| MB³/RA | 226 Gm+ cocci $1.0 \times 10^6$ Expl. cocci | 35 | Negative |
| LW/RA | 200 Gm+ cocci | 5 | Negative |
| LW²/RA | 18,000 Gm− cocci | No growth (antibiotics) | |
| MC Classic urinary tract infection | $7.9 \times 10^6$ Gm− rods | $6.6 \times 10^3$ | |
| SP/RA | $2.9 \times 10^6$ Gm+ rods | 4,200 (Blood Agar Plate) 2,600 (phenyl ethanol B.A.P.) | |
| SP²/RA | 0 (on antibiotics) | 0 | Negative |
| LS/RA | $1.8 \times 10^6$ Gm+ rods | 4,700 (Blood Agar Plate) 2,600 (Phenyl ethanol B.A.P.) | |
| EP Classic Urinary Tract Infection | $1 \times 10^6$ Gm− rods | $3 \times 10^5$ | |
| JM/hypertension | 70 Gm+ cocci Expl. cocci++ | 5 | |
| JH Ankylosing Spondylitis | 2,000 Gm+ cocci | | |
| BC | 50 Gm+ cocci | No growth | |

TABLE VI-continued

QUANTIFICATION OF BACTERIA AND BACTERIAL FRAGMENTS OBSERVED

| Patient/ Diagnosis | Microscopic Evaluation Bacteria per ml. | Culture Colonies/ml. | Routine Hospital Culture |
|---|---|---|---|
| retinal edema arthralgia | | 5 days aerobic and anaerobic | |
| BC/RA | 3,400 Gm+ cocci | 200 | Negative |
| MF/Osteoarthritis | 10 Gm+ cocci | 1 | |

N.B. Large Gm+ cocci grow easily and they correlate less well with illness.

Results presented in Table IV clearly indicate that the present methods may be used as a rapid screening procedure to determine not only the type of bacteria, but also to estimate the bacterial count, and to ensure that a fastidious one is not overgrown and lost.

The present microscopic method has important advantages over both the aerobic and anaerobic culture methods used conventionally.

NOVEL METHODS FOR TREATMENT OF RHEUMATOID ARTHRITIS

As explained above, in numerous cases of rheumatoid arthritis, large numbers of small cocci have been detected in urine samples. Typical photomicrographs often reveal hundreds of cocci per oil immersion field. Patients have had significant improvement of the illness on antibacterial therapy to greatly reduce or eliminate the cocci without any other change in their medication. Some have even had a full remission of the illness with eradication of the bacteriuria.

Among the most useful therapeutic agents, the antibiotics lincomycin and clindamycin, alone or with aminoglycoside antibiotic such as streptomycin, tobramycin, kanamycin, neomycin, or amikacin, seem to be the most useful. Other useful therapeutic agents are cephalexin, cephradine, cefazolin, cephalothin, chloramphenicol, novobiocin, fusidic acid, the quinolones, metronidazole, and some of the penicillins. More antibacterial agents may also be found to be useful, and the methodology described herein is valuable to determine whether any given agent or new agent is effective in-vivo. When the drugs are given parenterally, the dosage can be controlled and the response has been predictable. With clindamycin, 600 to 900 mg ( and in some instances more than 2400 mg) can be given by mouth daily. With oral lincomycin gastrointestinal absorption is more limiting. Better and more predictable results are had by intravenous administration of about 6.0 to 8.4 gm per day clindamycin, or 9.0 to 18 gm per day of lincomycin. The drug dosage is continued at least until the urine sediment, examined by the methods as disclosed above, no longer shows the presence of cocci.

Novel Methods for Treating "Essential" Hypertension and Other Conditions

According to the present invention, large numbers of cocci or "exploded cocci" have been detected in urine samples from persons suffering from "essential hypertension". Antibiotic therapy appropriate for such microorganisms, usually given in an analogous protocol over a long time, offers therapeutic benefit for "essential hypertension" found to be associated with bacteriuria.

In addition, other conditions of hitherto unknown or uncertain etiology have been associated with bacteriuria. Application of antibiotic therapy appropriate for the microorganisms detected not only diminishes these organisms, but also offers therapeutic benefit for the underlying disease. Conditions found to be associated with bacteriuria and which have been beneficially treated with antibiotic therapy according to the present invention are listed above (vide supra). They include: syndromes related to rheumatoid arthritis such a Reiter's disease, ankylosing spondylitis, bursitis, tendonitis, temporo-mandibular arthritis, sacroiliac arthritis, carpal-tunnel syndrome, temporal arteritis, other arteritis, palindromic rheumatism, etc.; classic migraine, osteoarthritis with pain, Crohn's disease; mitral valve prolapse, with or without arrhythmias, and with or without associated "transient ischemic attacks" involving the central nervous system; rheumatic fever without evidence of the presence of the group A Streptococcus haemolyticus; systemic lupus erythematosis; scleroderma; and transient ischemic attacks of the central nervous system.

Moreover, Gram positive bacteria have been found in the urine from patients suffering from a variety of renal disorders, including: renal failure associated with congenital polycystic kidneys; renal failure due to otherwise unspecified "chronic nephritis"; "brittle" diabetes mellitus; recurring kidney stones; unexplained proteinuria; unexplained brawny edema of the legs; and chronic brawny edema (i.e., lymphangiitis or elephantiasis not due to non-bacterial parasites). Antibiotic therapy which reduced or eliminated the bacteriuria, and benefited the patients as much as or more than it would had they been suffering the now-classic pyelonephritis.

The antibiotics of the lincosamine group (lincomycin and clindamycin), alone or in combination with an aminoglycoside such as streptomycin, tobramycin, kanamycin, neomycin, or amikacin seem to be the most useful. Other beneficial therapeutic agents include the antibiotics cephalexin, cephradine, cefazolin, chloramphenicol, novobiocin, metronidazole, fusidic acid, the quinolones, and the penicillins. When the antibiotics are given parenterally, the dosage can be better controlled. Other routes of administration, however, are also useful. With clindamycin 600 to 3600 mg (or even more) can be given by mouth daily. Lincomycin is less well tolerated by mouth. Other lincosamines may be useful. More predictable results are obtained by intravenous administration of about 2.4 to 8.4 gm of clindamycin or 9 or 24 gm of lincomycin per day.

Examples; Treatment of Patients Suffering Rheumatoid Arthritis

EXAMPLE I

JNF is 58 years old. She began having arthritis in her left knee, right foot, and right hand, and then bursitis in the left shoulder. She received non-steroid anti-arthritic medications with limited success. In 1980, an orthopedic surgeon injected a corticoid into her right elbow with good relief. She first noticed a rheumatoid nodule at the base of her left index finger. When seen, she also had a trace of edema i both legs. Her stained urinary sediment contained large numbers of encapsulated diplococci. On oral cephalexin (at a dosage of 1 gm per day) and ibuprofen, she realized major relief in a week. The cephalexin was continued. In two months the rheumatoid nodule began to shrink and it disappeared several months later. At three months, she only required 400 mg of ibuprofen a day to control her arthralgia. That month the diplococci reappeared and she had a mild flare-up. Both responded to five days of clindamycin and then cephalexin was resumed. Since then she has had only a few mild flare-ups, each associated with a bacteriological relapse and each responding to a change in the antibiotic, usually to clindamycin, followed by resumption of cephalexin.

EXAMPLE II

GC was a 47-year old with 22 years of severe RA when first seen by applicant, and hospitalized for antibacterial therapy. She had had virtually every known therapy including courses of gold, penicillamine, immunosuppressants, 60 mg/day of prednisone, non-steroidal anti-rheumatics, and acupuncture in a London clinic. She had had fifteen operations to replace ten joints and two more joint replacements had been recommended. She was in constant pain. Her urine contained large numbers of small streptococci. Routine urine culture was negative. Hemoglobin 11.6 g/dl, wbc 11,900/cmm, RA factor negative, and ANA only +1 undiluted. Complement C3 and C4 were normal and the IgG was slightly low. She was given 1.8 gm of clindamycin and 1 gm of cefamandole daily by a continuous I.V. drip and maintained on the prior medications. In one week she was asymptomatic and discharged on the same medications plus clindamycin. After she began to walk she fell and fractured her hip. The hip was replaced elsewhere. Antibacterials were discontinued. About five months later, she had a bacterial relapse followed by a clinical relapse. Again she had good relief on antibiotics, but she continued to relapse until one day she fell, sustained a shoulder fracture and was hospitalized elsewhere.

EXAMPLE III

SMcC was a 24-year old, who had fatigued easily for several years, had recurrent back pain primarily in the sacroiliac area, and had episodes of epigastric pain with nausea and persistent vomiting. She had been followed by subspecialists in medicine since she was a nursing student and she had been hospitalized by a gastroenterologist because of the same trouble. No diagnosis had been established. Non-steroidal anti-arthritis medicines offered minimal benefit. A catheterized urine showed small cocci and a culture grew out between 6,000 and 50,000 colonies of a diphtheroid that was sensitive to multiple antibiotics. (Microorganisms can become distorted in a hostile environment such as urine, but it is believed that the organisms photographed under the microscope are much more likely to be streptococci than diphtheroids). In a continuous I.V. drip, she received 2.4 gm clindamycin and 2.0 gm cefazolin per day for one week. All symptoms disappeared except the pain of sacroiliac arthritis. That was relieved by intra-articular injection of a corticosteroid. Soon after discharge, she lost nine pounds of edema, regained her stamina, and began working 16-hour shifts. The abdominal symptoms have never returned. She has had one relapse of malaise preceded by a bacterial relapse. Her urine often contains Gram positive rods which give her only mild bladder symptoms. One relapse of sacroiliac arthritis required another intra-articular injection of steroids. She is clinically well and she takes no anti-arthritic medication.

EXAMPLE IV

ClaF is a 50 year old, with seven years of progressive painful RA in multiple joints, progressive deformity of her hands and swelling of her knees. She had been treated by many physicians, including two rheumatologists, and she had received virtually every modality of therapy, including gold, penicillamine, methotrexate, plaquenil, steroids, etc. She had been gastroscoped for sequelae of non-steroidal anti-rheumatics. She had become depressed and suicidal. Since her first pregnancy 26 years before, she had used diuretics for swelling of her legs. She got up to urinate 3–4 times a night. Admission urine examined according to the present method showed small encapsulated diplococci which are probably streptococci. The corresponding hospital urine culture showed no growth. Her RA titer 1:160, ANA 1:2500, and sedimentation rate 110/hr. She had inflamed meticarpophalangeal (MP) joints of her hands (knuckles), there was ulnar deviation of the fingers typical of RA, the knees were swollen and there was a large rheumatoid nodule beneath the left great toe. She was given 2.4 gm of clindamycin with 1 gm of nafcillin by vein per day and maintained on her previous medication which included 10 mg per day of prednisone. On the third day, her urine contained no bacteria and she was free of pain. On the 10th day, she was discharged on 600 mg of clindamycin and 10 mg of prednisone a day. After two weeks, she had a recurrence of the Gram positive diplococci along with casts in her urine, and this was followed by a minor relapse of her arthritis. Cephalexin and tetracyline failed to influence either the urine finding or the clinical course and one week later she had 100 mg/ml proteinuria. She was given tobramycin and lincomycin I.M. and clindamycin and 6 mg/day of aspirin by mouth for a week with a brief bacteriological remission and brief clinical improvement. Ampicillin with dicloxacillin was without effect. Clindamycin at 600 mg/day by mouth for a month resulted in some improvement, but she again relapsed. Cloaxacillin and then nitrofurantoin did not effect either the urine sediment or the symptoms. She was bothered by sinusitis. Four months after hospitalization she was again started on 1.2 gm a day of clindamycin by mouth with disappearance of the cocci from the urine and significant clinical improvement. Off clindamycin she again had a bacteriological and a clinical relapse. There may have been some improvement on sulfasozazole with trimethoprim, but in two weeks she again required hospitalization.

She was hospitalized and given 1.8 gm of clindamycin a day I.V. for one week, again with complete relief of pain and swelling. Her RA assay, previously positive 1:160, had become negative, and her ANA was still normal. She was discharged on cephradine. One month later her clinical improvement continued and the rheumatoid nodule became much smaller and softer, but she had a bacteriological relapse. Oral clindamycin at 600 mg/day was ineffective and she was hospitalized again. Her RA was positive 1:10 and her erythrocyte sedimentation rate was 41 mm/hour. She had a bacteriological and clinical remission of 1.2 gm/day of clindamycin I.V., and she was discharged on 900 mg/day of clindamycin by mouth.

Following mild sinusitis and in spite of oral clindamycin at 600 mg/day, she again required hospitalization. Her RA was now positive in a dilution of 1:2560, and her erythrocyte sedimentation rate was 110 mg/hour. The ANA remained negative. Again on clindamycin at 1.2 gm/day by vein, she felt better in 48 hours and she had a clinical and bacteriological remission. She was given 100 mg/day of azathioprine in the hope of reducing the auto-immune response. One day after discharge she noted swelling of her left leg and dicoumarol was begun. The leg problem subsided. Two months later, in spite of oral clindamycin at 600 mg/day and cephradine at 1 mg/day she again required hospitalization following 1 week of a flu-like illness. Her joints swelled and 10 ml of bloody fluid was removed from her right knee. The joint fluid was devoid of bacteria by stain and by culture. She had a wbc of 18,000/ml but her RA was positive only to a dilution of 1:20 and the ANA remained negative, She had developed diabetes mellitus and required insulin for the next two months only. Again she was given intense antibiotics including 1.2 gm/day of clindamycin. She was discharged on 600 mg/day of clindamycin by mouth and she has not been hospitalized since.

She began to relapse again, and by October she was in severe pain. Under the belief that the streptococcus seen in her urine before each flare-up of arthritis (and since isolated from her urine) was indeed the source of antigen that provoked the auto-antibodies that caused inflammation of her joints, it was postulated that some component of that streptococcus provoked an antibody that cross-reacted with her joint tissue. If that component were within the streptococcus, the destruction of the streptococcus would liberate the component slowly but steadily in the natural disease, but massive clindamycin or lincomycin would liberate a large dose of antigen which would act like a booster shot. Thus, instead of repeated hospitalizations (which she began to refuse), an attempt was made to give her a large dose of lincomycin (to destroy the streptococcus), along with a large bolus of cyclophosphamide to eliminate the "booster" effect. She was given her first I.V. of 1.2 gm lincomycin with 0.5 gm cyclophosphamide. Except for two doses of 1.0 gm of cyclophosphamide this was repeated at weekly intervals to a total of 9 sessions of I.V. therapy with 7.5 gm of cyclophosphamide. She takes 600 mg/day of clindamycin by mouth also. She has been free of symptoms since the onset of this treatment and her urine has been free of streptococci.

In summary, a 50-year-old with severe, rapidly progressing arthritis had six remissions on brief courses of 1.2 to 2.4 gm/day of clindamycin by vein in the hospital, but relapsed on oral clindamycin and on other antibiotics. Finally, she had been in a prolonged remission using I.V. lincomycin with cyclophosphamide at increasing intervals. Diabetes mellitus appeared briefly in the period before cyclophosphamide, but her blood sugar returned to normal without insulin in two months.

EXAMPLE V

SSB is a 32-year-old woman who had surgery for partial obstruction of the right ureteropelvic junction at age 12. For the next many years he had recurrent "bladder infections". At age 24 she began to have periods of headaches, malaise, weakness, arthralgia, and leucopenia. Sometimes she also had tiny sterile abscesses in her skin, even in the thick palmar skin. On each of these occasions, her urine contained large numbers of tiny cocci which failed to grow in cultures. The organisms are stained by a fluorescent dye which glows yellow to orange when bound to nucleic acids. The pattern of nucleic acids clearly outlines the small cocci. Her ANA titer rose to 1:80. The RA test remains negative. A radioisotope "triple renal scan" was normal. EAch of the episodes quickly responded to intravenous lincomycin or clindamycin at a dosage level of 1.8 to 2.1 gm/day given with cefazolin.

EXAMPLE VI

TK is a 28-year-old. He complained of three months of progressive pain and swelling in the joints of his hands and in his previously injured knee. The onset was insidious and without warning. He had no other symptoms. The diagnosis elsewhere was RA. His urine contained cocci. On clindamycin and ibuprofen he had a remission in one week, but his urine continued to show "exploded" cocci. This finding cleared following a single initial injection of 0.6 gm. of lincomycin and 600 mg./day of cyclophosphamide administered orally for six days. He was maintained on tetracycline for four months and he has been asymptomatic since.

EXAMPLE VII

EJRH is a 59-year-old, with two years of progressive arthritis beginning in his left shoulder and within a few months continuing in almost every joint in his body, including the temperomandibular joints, hips, knees, shoulders, elbows, wrists, and fingers. He also had a one-year history of bilateral kidney stones. He had received iron shots and vitamins for his anemia. When he arrived, he was taking naproxen and 10 mg prednisone a day without relief of the pain or swelling. Physical examination revealed evidence of arthritis of all of the above joints. The applicant found streptococci in his urine, but the routine hospital laboratory reported no growth in the urine culture. He was mildly anemic with a hemoglobin of 11.2 mg%. His erythrocyte sedimentation rate was 101 mm/hour. The C reactive protein was positive. The RA was positive to a titer of 10,240 and the ANA to a titer of 1:5,120. The serum albumin was low at 2.5 gm%. The IgM was elevated, at 503 mg% (normal 75-125), IgA at 398 mg% (normal 150-250), and IgE t 490 u/ml (less than 122). The complement C-3 was normal, the C-4 marginally low, and the CH-50 was low at 30 u (normal 60-120). Pyelograms showed an atrophic left kidney and the right renal stones. He was given 1.8 gm clindamycin and 1.0 gm cefazolin per day by vein and 160 mg tobramycin I.M. for 5 days. Prednisone was continued at 10 mg per day and the non-steroidal anti-inflammatory drug was continued. A rapid remission of arthritis began within 24 hours and within three days he was symptom free. His appetite and energy returned. On the 6th day, a renal stone blocking the ureteropelvic function was surgically removed. Recovery was uneventful.

At 2 months, he had some swelling of several joints on awakening. The swelling would subside by mid-morning. His urine showed cocci and he was given clindamycin 600 mg/day for seven days. At 4 months he had residual shoulder pain. He had regained six pounds and his color was better. He was again given clindamycin. He passed another renal stone. At 7 months and at 9 months he was without symptoms. He was still slightly anemic at 7 months.

EXAMPLE VIII

CS was a 39-year-old who began having arthritis in the proximal interphalangeal joints, hips, knees, and back about four years before applicant first saw her. She complained of nocturia, a few times a night for several years.

She was admitted to a hospital in Alexandria, Va., complaining of severe low back pain radiating to thighs and to abdomen. It was aggravated by extension of her back but by no other motion. She gave a past history of recurrent urinary tract infections. On the second admission, she had mononucleosis also. No lab test was done for RA except for a bone scan which was negative. Her back pain was attributed to extensive ballet lessons. Because of the X-ray changes in the spine the discharge diagnosis was Degenerative Arthritis. She was given naproxen, a non-steroidal anti-arthritic.

She was hospitalized in Oberlin, Ohio where she was diagnosed clinically as having "chrondritis" in her chest and she was given naproxen again. Her ANA, ASO, and C reactive protein were normal. Upper GI X-rays, gastroscopy, barium enema, EKG., etc. were also normal.

On physical examination she was found to have fusiform swelling of her fingers due to inflammation of the p.i.p. joints.

Her urine showed a few diplococci and +++"exploded cocci". A course of cephalexin was without benefit. A few Gram negative rods appeared in her urine and a course of ampicillin and cinoxacin eliminated the rods, but the cocci remained and the arthritis got worse. Trimethoprim with sulfasoxazole was without benefit, and tetracycline caused nausea. Seven months after I first saw her she had acute sacroiliac arthritis, and the normal curvature of her lumbar spine had reversed. The cocci persisted in her urine on microscopic examination.

She was admitted to the Touro Infirmary in New Orleans where a routine urine culture was negative, her white blood count was low at 3,400/mm$^3$ and her ANA was positive to a titer of 1:80. Complement C-3 and C-4 levels were both reduced. Other tests bearing on RA were negative. X-rays of the spine showed only degenerative changes. She was given 1.8 gm/day of clindamycin I.V. for 3 days and then 600 mg/day by mouth, and she was also given 160 mg/day of tobramycin for 5 days. By the fifth day she had become free of all symptoms and she was discharged on oral clindamycin, 600 mg/day. When seen 1 month later she was still on clindamycin and she was doing well. Three months later she returned in a relapse. She had discontinued the antibacterial agent and had begun prednisone at 20 mg/day. Her fingers were again swollen and her back trouble had returned. Her urine contained 30 mg% protein, cellular casts, and cocci. She was again hospitalized.

Her admission urine culture was reported as showing no growth. Her white blood count was low to 2,700/mm$^3$ and rose to 4,800/mm$^3$. She was anemic with a Hct as low as 31.6%. The ANA was again positive at 1:80, the complement C-3 and C-4 were both low again. The IgG was low and the IgM was slightly high. All other tests for RA were negative again. She was given a continuous I.V. drip containing 1.8 gm of clindamycin and 1.0 gm of cefamandole a day, and she was given 160 mg/day of tobramycin. On the fifth day she was discharged completely asymptomatic. Discharge medications were prednisone reduced to 15 mg/day, naproxen and 600 mg/day of clindamycin.

Two follow-up urines were devoid of cocci. She went to another city. Later she wrote that she had a relapse.

Examples: Treatment of Patients Suffering "Essential" Hypertension

Using the methods of the present invention, most cases of essential hypertension have been found to excrete significant numbers of cocci in the urine. The cocci associated with this disorder are often different from those seen in patients suffering the rheumatoid illnesses in that they tend to be larger, suggesting Staphylococci, and there is often a preponderance of forms that are compatible with the electron photomicrographs in the literature of cocci that have exploded after exposure to some antibiotic or to some immune mechanism. For convenience, these forms are referred to as "exploded cocci". They may be different species, such as staphylococci instead of streptococci. Similar forms have been produced by (a) isolating the cell walls of healthy streptococci or staphylococci that have been grown in broth in the laboratory and (b) by staining those isolated cell walls using the method described herein. That these microorganisms are in the chain of causation of the hypertension is demonstrated by ridding the patient of the cocci by antibiotic treatment and observing the patient's improvement either in terms of lessening the need for antihypertensive drugs or eliminating the need of antihypertensive drugs. The preferred drug dosage levels are often the same as above described with respect to RA, but these patients are more likely to respond to anti-staphylococcal cephalosporins, and relief of hypertension may be slower.

EXAMPLE IX

At age 30, WS had a period of hypertension that went away. At age 57 he noted increasing fatigue in his daily jogging in the park. His Blood Pressure (BP) was 190/140. He began 50 mg of chlorthalidone a day and increased it to 100 mg a day with some drop in his pressure but he became weak. On examination his BP was 150/100. He was overweight and his retinal arterioles were slightly narrowed. X-ray of the chest was normal. An EKG showed low T waves. The serum sodium was 131 meq/l and the potassium 4.1. The urine showed hyaline casts, Gram positive and negative cocci, and "exploded cocci". Chlorthalidone was administered at a dosage of 100 mg/day for 3 days and clindamycin at a dosage of 600 mg/day for 7 days was added. Three days later his BP was 118/80. Ventricular premature beats cleared on an oral potassium supplement. At one week he was given cephalexin at a dosage of 1 mg/day for seven days because a few cocci remained in the urine. At three weeks he became weak with a BP of 110/70. Chlorthalidone was reduced to 50 mg per day and quinidine was given for recurrence of his ventricular premature beats. A trace of proteinuria temporarily increased to 30 mg% proteinuria. Trimethoprim at a dosage of 200 mg/day was substituted for cephalexin because of continued "exploded cocci". At six weeks he was clinically well with a BP of 110/74. Proteinuria was reduced to normal and a few cocci remained. Chlorthalidone was reduced to 25 mg per day and cephalexin was restarted. At three months he was well, his BP was 110/74, his urine was free of bacteria, and he took 25 mg chlorthalidone only at his whim.

EXAMPLE X

CH is 35 years old. Without symptoms he discovered that his BP was 165/120. Repeat determinations were similar. On 2 mg per day of prazosin his blood pressure fell to 130/78 but he fatigued more easily and in slow jogging his pulse rate rose to 105 per minute. At rest his pulse rate was high. Physical examination revealed only normal findings. His urine contained only a trace of protein. The sediment contained no formed elements, but it showed + + encapsulated cocci and + + "exploded cocci". Prazosin was stopped and he was given cephalexin at a dosage of 1.5 gm/day. Eight days later only a few cocci remained. In two weeks his blood pressure was normal and it has remained so to date. At three weeks he had 30 mg% proteinuria and + + + "exploded cocci". On 600 mg/day of clindamycin and other cephalosporins for seven days the proteinuria stopped, but he still shows cocci in the urine on occasion. After two or three months of antibiotic therapy, he noted a return of his sense of well being and stamina, his resting pulse rate is 56 to 60, and jogging does not cause a tachycardia.

EXAMPLE XI

TM is an obese 58-year-old. In 1966 in a routine physical examination at work he was found to have a BP of 240/120. His only symptom was nocturia. On antihypertensive medicines he began to have headaches and visual difficulty. When I first saw him seven months later his BP was 240/160, he had flame-shaped retinal hemorrhages, 300 mg% proteinuria, mild azotemia, and innumerable small cocci in the sediment. On 75 mg/day of hydrochlorthiazide the pressure fell to 190/110 but the symptoms persisted. Intramuscular nafcillin caused a spell of weakness with a blood pressure of 160/90. (It is possible that this was a Herxheimer reaction because TM was not and is not allergic to nafcillin or to any other penicillin). After three weeks on 1 gm per day of novobiocin he was asymptomatic with a BP of 130/70, with 750 mg of methyldopa and 75 mg of hydrodiuril a day. After five weeks of therapy his retinal hemorrhages had stopped and the retinal arterioles appeared normal. At two months his blood pressure had fallen to 100/66. His methyldopa was reduced to 500 mg/day and hydrodiuril to 50 mg/day. Cloxacillin was continued. At six months the BP was 10/70 and hydrodiuril was reduced to 25 mg/day. At two years he was off all antihypertensive therapy and his blood pressure remained in the range of 120/80 to 140/90. To date he has had no restriction to dietary sodium. Two and one-half years after first seen, he had staphylococci in his urine and his blood pressure rose to 150/100. On resuming a dosage of 1 gm per day of a staph-specific penicillin it fell to 130/80. Some time later he had become obese and he again had staphylococci in the urine. It was necessary to resume antihypertensive therapy for several months. He later developed diabetes. "Exploded cocci" reappeared and have since been difficult to eliminate. He had a myocardial infarction with persistent angina. Since that time he has to take as much as 750 mg of methyldopa and 50 mg hydrodiuril a day. He developed gout, but he has not changed his eating habits. (16 years) his blood pressure was 140/80, height 5 feet 6 inches, weight 197 lbs., and he was taking allopurinol, antiangina drugs, penicillin, and the same doses of above drugs for hypertension. In summary TM had a prolonged remission on antibiotic therapy alone and now, he is still on low doses of antihypertensives.

EXAMPLE XII

WR is a 67-year-old who has had back pain intermittently since his college days. He consulted the applicant because of 1 month of pain in his ankles followed by pain and swelling of his knees which prohibited him from gardening. He was taking 20 mg/day of piroxicam with minimal relief of pain. He had had hypertension for 20 years controlled to 160/90-95 by 2 mg of prazosin and 50 mg of atenolol daily. On examination his BP was 220/110 but it fell with rest to 140/80. The only abnormal finding was a swelling of the left knee. His urine showed a few tubular epithelial cells and only a few encapsulated diplococci. Prazosin was stopped and clindamycin at a dosage of 600 mg/day for seven days was started. After one week he felt better and his BP was 136/72. His urine showed an occasional diplococcus and + + + "exploded cocci". On 1 gm/day for 10 days of cephalexin the BP fell to 112/66 and his atenolol was reduced to 25 mg/day. At four months he was off all antihypertensive medicines and his blood pressure rose to 160/90. Antihypertensives were resumed for only 1 month. When discontinued the BP remained normal. When seen most recently his BP was 140/80. He stated that he felt better than he had in many years, and that he had given up wine which he had drunk only to feel better. He lost seven pounds. Now he has no arthralgia or joint swelling, but he elects to continue the piroxicam. He is concerned only that his potency has not returned.

EXAMPLE XIII

JSG is a tense, overweight businessman with hyperlipemia who was taking 10 mg of bendroflumethiazide daily when first seen. Physical examination and EKG were normal, but his urine contained a trace of protein and staphylococci, both free and in casts. On 1.5 gm/day of oral cephalexin and no thiazide his BP fell to 120/78. He has been on cephalexin at a dosage of 1 gm per day almost continually since, because he feels better on the drug. He has had two attacks of true vertigo which responded to thiazides and ammonium chloride. Alternate antibiotics were given for the associated upper respiratory infection. His BP has only once risen above normal and then briefly. All chemical screening is normal except for the lipids. He remains very active and does not follow any diet.

The enumeration of specific diseases above should not be taken to limit the disclosed method in a clinical context as a guide to when antibiotic therapy may be appropriate.

I claim:

1. In a method for direct microscopic detection of bacteria or bacterial fragments in a urine sample including the steps of staining the bacteria or bacterial fragments with an aqueous soluble dye and microscopically observing the bacteria, wherein the improvement comprises centrifuging the sample at about 3,500–11,000 times gravity to obtain a sediment comprising bacterial or bacterial fragments in the sample prior to staining.

2. The method according to claim 1, wherein the urine sample contains the lipid soluble components which are removed by use of a lipid solvent composition.

3. The method according to claim 2, wherein the lipid solvent composition is a mixture of methanol and halogenated hydrocarbon, or methanol alone.

4. The method according to claim 3, wherein the lipid solvent composition is a mixture of methanol and 1,1,1-trichloroethane.

5. The method of claim 1, further comprising contacting the sediment with a tagged anti-human IgG antibody to demonstrate the presence of human IgG on bacteria in the sediment.

6. The method of claim 5, wherein the antibody is tagged with a fluorescent dye.

7. The method in claim 1, wherein the sediment is contacted with an acridine dye to demonstrate nucleic acids by fluorescence.

8. The method in claim 1, further comprising contacting the sediment with a proteolytic enzyme.

9. The method of claim 8, wherein the proteolytic enzyme is selected from group consisting of bacterial proteases fungal proteases, crystalline trypsin, and chymotrypsin.

10. The method of claim 1, further comprising contacting the sediment with an enzyme selected from the group consisting of amylases, DNases, RNases, lipases, lecithinases, sialases, neuraminidases, hyaluronidases and sphingomyelinases.

11. A method of treating rheumatoid arthritis in a human, comprising:
(a) detecting abnormal bacteria or bacterial fragments in a urine sample from a human suffering from rheumatoid arthritis according to the method of claim 1,
(b) administering a therapeutically effective amount of an antibiotic effective against the bacteria detected in step (a); and
(c) monitoring the urine for the presence of bacteria or bacterial fragments according to the method of claim 2 to determine efficacy of the treatment.

12. The method of claim 11, wherein the antibiotic is selected from the group consisting of clindamycin, lincomycin, cefazolin, cefamandole, cephradine, cephalexin, cephalothin, moxalactum, fusidic acid, novobiocin, penicillin, piperacillin and quinolones.

13. The method according to claim 12, further comprising administering an additional antibiotic selected from the group consisting of streptomycin, tobramycin, kanamycin, neomycin, and amikacin.

14. The method according to claim 1, further comprising washing the sediment with a sterile particle-free aqueous solution slightly hypertonic to normal serum prior to staining.

15. The method according to claim 1 further comprising the steps of treating the sediment with a protease to remove insoluble proteins adhering to the bacteria, and centrifuging the treated sediment at about 3,500 to 11,000 times gravity prior to staining.

16. A method of treating essential hypertension in a human comprising:
(a) detecting abnormal bacteria or bacterial fragments in a urine sample from a human suffering from essential hypertension according to the method of claim 1,
(b) administering a therapeutically effective amount of an antibiotic effective against the bacteria detected in step (a); and
(c) monitoring the urine for the presence of bacteria or bacterial fragments according to the method of claim 2 to determine efficacy of the treatment.

17. The method of claim 2, further comprising exposing the sediment to a labeled antibody.

18. The method of claim 2, further comprising exposing the sediment to a fluorescent dye.

19. The method of claim 18, in which the fluorescent dye comprises acridine orange.

20. The method of claim 2, further comprising exposing the sediment to an enzyme prior to microscopic examination.

21. The method of claim 20, in which the enzyme is selected from the group consisting of amylases, DNases, RNases, lipases, lecithinases, sialases, neuraminidases, hyaluronidases, sphingomyelinases, bacterial proteases and trypsin.

22. A method of detecting bacteria or bacterial fragments in a urine sample, comprising:
(a) centrifuging the sample at a relative centrifugal force of about 3,500–11,000 times gravity to sediment bacteria and bacterial fragments;
(b) separating the sediment from the supernatant;
(c) spreading the sediment on a surface;
(d) washing the sediment on the surface with a lipid solvent composition to remove any lipid components of the sediment preparatory to staining;
(e) fixing and staining the washed sediment; and,
(f) microscopically observing the washed and stained sediment.

23. A method of diagnosing and treating rheumatoid arthritis or essential hypertension in a human comprising:
(a) obtaining a urine sample from the human;
(b) preparing the urine sample for microscopic examination by centrifuging the sample at about 3500–11000 times gravity, separating the sediment from the supernatant, spreading the sediment on a surface, washing the sediment with a lipid solvent to remove any lipid components of the sediment, fixing, and staining the washed sediment;
(c) microscopically detecting and identifying any bacteria or bacterial fragments in the stained sediment;
(d) administering to the human a therapeutically effective amount of an antibiotic effective against the bacteria identified in step (c); and
(e) monitoring the treatment by periodically repeating steps (a), (b), and (c) while continuing the treatment of step (d) until the performance of step (c) shows the substantial absence of the identified bacteria.

24. A method as identified in claim 23, wherein the antibiotic amount is at least 600 mg./day.

25. A method as defined in claim 23, wherein the antibiotic is a lincosamine.

26. A kit for preparing urine sediment for examination consisting essentially of:
(a) a container of a lipid removing solvent, 0.03 to 5 volume percent 1,1,1 trichloroethane in absolute methanol,
(b) a container of a fixative containing about 0.004 to 0.4 volume percent glutaraldehyde in methanol,
(c) a container of an acidified methanolic solution of alcian blue,
(d) optionally, containers for the Gram stain, including:
(1) a container of an aqueous solution of crystal violet,
(2) a container of elemental iodine dissolved in aqueous potassium iodide,
(3) a container of a destaining solution,
(4) a container of a counterstain, and,
(e) optionally, a container of a solution to wash the sediment which consists of an aqueous solution of sodium chloride and a dilute solution of acidified alcian blue.

* * * * *